(12) United States Patent
Kisak et al.

(10) Patent No.: US 9,579,296 B2
(45) Date of Patent: *Feb. 28, 2017

(54) COMPOSITIONS AND METHODS FOR TRANSDERMAL DELIVERY OF HORMONES AND OTHER MEDICINAL AGENTS

(71) Applicant: Teikoku Pharma USA, Inc., San Jose, CA (US)

(72) Inventors: Edward Kisak, San Diego, CA (US); Nadir Buyuktimkin, San Diego, CA (US); Servet Buyuktimkin, San Diego, CA (US); John Newsam, La Jolla, CA (US); Jianye Wen, Los Gatos, CA (US); Jutaro Shudo, San Jose, CA (US); Amit Jain, Milpitas, CA (US)

(73) Assignee: Teikoku Pharma USA, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/837,439

(22) Filed: Aug. 27, 2015

(65) Prior Publication Data

US 2016/0051487 A1    Feb. 25, 2016

Related U.S. Application Data

(63) Continuation of application No. 14/135,770, filed on Dec. 20, 2013, now Pat. No. 9,144,553.

(60) Provisional application No. 61/740,879, filed on Dec. 21, 2012.

(51) Int. Cl.
| | | |
|---|---|---|
| A61K 9/70 | (2006.01) |
| A61K 47/32 | (2006.01) |
| A61K 47/12 | (2006.01) |
| A61K 47/14 | (2006.01) |
| A61K 31/565 | (2006.01) |
| A61K 31/567 | (2006.01) |

(52) U.S. Cl.
CPC .......... *A61K 9/7061* (2013.01); *A61K 31/565* (2013.01); *A61K 31/567* (2013.01); *A61K 47/12* (2013.01); *A61K 47/14* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 4,816,258 A | 3/1989 | Nedberge et al. |
| 5,296,230 A | 3/1994 | Chien et al. |
| 5,512,292 A | 4/1996 | Gale et al. |
| 5,560,922 A | 10/1996 | Chien et al. |
| 5,762,956 A | 6/1998 | Chien et al. |
| 5,788,983 A | 8/1998 | Chien et al. |
| 6,024,974 A | 2/2000 | Li |
| 6,118,020 A | 9/2000 | Buyuktimkin et al. |
| 6,825,234 B2 | 11/2004 | Yeager et al. |
| 7,045,145 B1 | 5/2006 | Chien |
| 7,384,650 B2 | 6/2008 | Chien |
| 7,468,470 B2 | 12/2008 | Bracht |
| 7,795,309 B2 | 9/2010 | Kisak et al. |
| 8,221,784 B2 | 7/2012 | Chien |
| 8,221,785 B2 | 7/2012 | Chien |
| 8,246,978 B2 | 8/2012 | Kydonieus et al. |
| 9,144,553 B2 | 9/2015 | Kisak et al. |
| 2004/0037873 A1 | 2/2004 | Anigbogu et al. |
| 2004/0053901 A1 | 3/2004 | Chien |
| 2005/0142175 A1 | 6/2005 | Langguth et al. |
| 2006/0121102 A1 | 6/2006 | Chiang |
| 2007/0065495 A1 | 3/2007 | Chien |
| 2007/0098722 A1 | 5/2007 | Bottazzi et al. |
| 2008/0300311 A1 | 12/2008 | Kisak et al. |
| 2009/0075963 A1 | 3/2009 | Levinson et al. |
| 2009/0098191 A1 | 4/2009 | Anderson et al. |
| 2009/0297590 A1 | 12/2009 | Yamaji et al. |
| 2009/0311312 A1 | 12/2009 | Chien |
| 2009/0324697 A1 | 12/2009 | Chien |
| 2010/0150993 A1 | 6/2010 | Theobald et al. |
| 2010/0178323 A1 | 7/2010 | Kydonieus et al. |
| 2010/0255072 A1 | 10/2010 | Kydonieus et al. |
| 2011/0251163 A1 | 10/2011 | Rossi et al. |
| 2011/0256210 A1 | 10/2011 | Rossi et al. |
| 2011/0268785 A1 | 11/2011 | Wen et al. |

FOREIGN PATENT DOCUMENTS

| | | |
|---|---|---|
| EP | 2316440 A1 | 5/2011 |
| WO | WO-01/37770 | 5/2001 |
| WO | WO-2006/036899 | 4/2006 |
| WO | WO-2010/054093 | 5/2010 |
| WO | WO-2011/014850 | 2/2011 |
| WO | WO-2011/028629 | 3/2011 |
| WO | WO-2011/041609 | 4/2011 |
| WO | WO-2011/044540 | 4/2011 |

(Continued)

OTHER PUBLICATIONS

Anonymous: "The Merck Index", 1996, Merck & Co., Inc., XP002722333, p. 935.
Archer et al., "Ethinyl estradiol and levonorgestrel pharmacokinetics with a low-dose transdermal contraceptive delivery system, AG200-15: a randomized controlled trial," *Contraception*, vol. 85, (2012), pp. 595-601.
Harrison, et al., "Simultaneous Estradiol and Levonorgestrel Transdermal Delivery from a 7-day Patch: In Vitro and In Vivo Drug Deliveries of Three Formulations," *Drug Development and Industrial Pharmacy*, vol. 33, (2007), pp. 373-380.
International Search Report and Written Opinion of the International Searching Authority, the European Patent Office, for PCT/US2013/076948, dated Apr. 8, 2014, 13 pages.

(Continued)

*Primary Examiner* — Richard Schnizer
*Assistant Examiner* — Katherine Peebles
(74) *Attorney, Agent, or Firm* — Goodwin Procter LLP

(57) ABSTRACT

The invention provides transdermal delivery systems, medical kits, and methods for using the transdermal delivery systems and kits for medical applications, such as delivery of contraceptive agents to control fertility.

22 Claims, 2 Drawing Sheets

(56) References Cited

FOREIGN PATENT DOCUMENTS

| WO | WO-2011/060195 | 5/2011 |
|----|----------------|--------|
| WO | WO-2011/063531 | 6/2011 |
| WO | WO-2011/079234 | 6/2011 |
| WO | WO-2011/088072 | 7/2011 |
| WO | WO-2011/112875 | 9/2011 |
| WO | WO-2011/149645 | 12/2011 |
| WO | WO-2012/065740 | 5/2012 |

OTHER PUBLICATIONS

Stanczyk et al., "Pharmacokinetics, tolerability and cycle control of three transdermal contraceptive delivery systems containing different doses of ethinylestradiol and levonorgestrel," *Horm. Mol. Biol. Clin. Invest.*, 6(2), (2011), pp. 231-240.

COMPOSITIONS AND METHODS FOR TRANSDERMAL DELIVERY OF HORMONES AND OTHER MEDICINAL AGENTS

RELATED APPLICATIONS

This application is a continuation of U.S. patent application Ser. No. 14/135,770, filed Dec. 20, 2013, which claims the benefit of and priority to U.S. Provisional Patent Application Ser. No. 61/740,879, filed Dec. 21, 2012, the entire contents of each application are incorporated herein by reference in their entirety.

FIELD OF THE INVENTION

The invention provides transdermal delivery systems, medical kits, and methods for using the transdermal delivery systems and kits for medical applications, such as delivery of contraceptive agents to control fertility.

BACKGROUND

Transdermal delivery of medicinal agents provides advantages over other routes of administration. For example, first-pass metabolism and variable rates of absorption associated with oral administration of medicinal agents can be avoided by transdermal administration. Intravenous injection and other methods of administering a medicinal agent by injection can cause pain upon insertion of a hypodermic needle into the patient. Transdermal administration can avoid pain at the site of administration and provide the further advantage that a medicinal agent can be administered continuously over several days without any continued action by the patient.

Multiple parties have investigated transdermal delivery of contraceptive agents to control fertility. See, for example, U.S. Pat. Nos. 5,296,230; 5,512,292; and 5,788,983. Advantages of transdermal delivery of contraceptive agents include improved patient compliance when using a multi-day, easy-to-use patch and reduced occurrence of over-dosing or under-dosing of the contraceptive agent, as can sometimes occur when patients are tasked with repeated oral administration of a contraceptive agent.

Transdermal delivery systems containing estrogens and/or progestins have been described. See, for example, U.S. Pat. Nos. 5,296,230; 5,512,292; and 5,788,983. One challenge for achieving effective contraception by transdermal delivery of an estrogen and/or progestin is the low skin permeability of many estrogens and/or progestins. Certain penetration enhancers have been described for increasing the rate at which certain medicinal agents permeate the skin. For example, U.S. Pat. No. 7,045,145 describes a combination of skin penetration enhancing agents that include dimethyl sulfoxide. However, transdermal formulations containing dimethyl sulfoxide suffer from various disadvantages, including malpleasant odors and potential complications during manufacturing of the transdermal delivery system due to the volatility of dimethyl sulfoxide. Further, the use of skin penetration enhancers in the transdermal delivery device can cause undesirable side effects, such as irritation of the patient's skin depending on the concentration and identity of agents used to increase skin penetration of the medicinal agent.

Therefore, the need exists for new transdermal delivery systems and methods for transdermally administering a medicinal agent. The present invention addresses this need and provides other related advantages due in part to the discovery of a novel combination of agents that increase the skin penetration rate of contraceptive agents levonorgestrel and ethinyl estradiol.

SUMMARY

The invention provides transdermal delivery systems, medical kits, and methods for using the transdermal delivery systems and kits for medical applications, such as delivery of contraceptive agents to control fertility. The transdermal delivery systems utilize a novel combination of agents that increase the skin penetration rate of medicinal agents, such as levonorgestrel and ethinyl estradiol. Various aspects and embodiments of the invention are described in further detail below.

One aspect of the invention provides a transdermal delivery system. The transdermal delivery system may comprise a backing layer affixed to an adhesive polymer matrix, where the adhesive polymer matrix provides for controlled release of at least one medicinal agent. To achieve controlled release, the adhesive polymer matrix comprises an adhesive polymer and at least two (preferably two or three) penetration enhancers selected from the group consisting of levulinic acid, glyceryl monooleate, lauryl lactate, isopropyl myristate, lactic acid, and pharmaceutically acceptable salts thereof. The identity and amount of the aforementioned penetration enhancers is selected in order to achieve the desired release properties for the medicinal agent(s) while minimizing the occurrence of adverse events, such as skin irritation caused by the adhesive polymer matrix. The adhesive polymer matrix may further comprise a humectant. An overlay layer and/or release liner may be used in the transdermal delivery system.

A more specific embodiment provides a transdermal delivery system comprising a backing layer affixed to an adhesive polymer matrix, wherein the adhesive polymer matrix comprises: (a) about 0.5% (w/w) to about 10% (w/w) of a first penetration enhancer selected from the group consisting of levulinic acid and a pharmaceutically acceptable salt thereof; (b) about 0.5% (w/w) to about 10% (w/w) of a second penetration enhancer selected from the group consisting of glyceryl monooleate and lauryl lactate; (c) an adhesive polymer; (d) a humectant; (e) levonorgestrel; and (f) ethinyl estradiol. This transdermal delivery system is useful for controlling fertility in a female subject. In certain embodiments, the first penetration enhancer is levulinic acid and the second penetration enhancer is glyceryl monooleate.

Another more specific embodiment provides a transdermal delivery system comprising a backing layer affixed to an adhesive polymer matrix, wherein the adhesive polymer matrix comprises: (a) about 3.5% (w/w) to about 4% (w/w) of a first penetration enhancer selected from the group consisting of levulinic acid and a pharmaceutically acceptable salt thereof; (b) about 2.2% (w/w) to about 2.8% (w/w) of a second penetration enhancer that is glyceryl monooleate; (c) about 86% (w/w) to about 90% (w/w) of an adhesive polymer that is a random copolymer of 2-ethylhexyl acrylate and vinyl acetate; (d) about 2% (w/w) to about 4% (w/w) of a humectant that is a copolymer of vinylpyrrolidone and vinyl acetate; (e) about 0.7% (w/w) to about 0.9% (w/w) levonorgestrel; and (f) about 0.7% (w/w) to about 0.9% (w/w) ethinyl estradiol.

Another more specific embodiment provides a transdermal delivery system comprising a backing layer affixed to an adhesive polymer matrix, wherein the adhesive polymer matrix comprises: (a) about 2.5% (w/w) to about 5% (w/w) of a first penetration enhancer selected from the group consisting of levulinic acid and a pharmaceutically acceptable salt thereof; (b) about 2.0% (w/w) to about 4% (w/w) of a second penetration enhancer that is glyceryl monooleate; (c) about 80% (w/w) to about 92% (w/w) of an adhesive polymer that is a random copolymer of 2-ethylhexyl acrylate and vinyl acetate; (d) about 2% (w/w) to about 4% (w/w) of a humectant that is a copolymer of vinylpyrrolidone and vinyl acetate; (e) about 0.6% (w/w) to about 1.0% (w/w) levonorgestrel; and (f) about 0.6% (w/w) to about 1.0% (w/w) ethinyl estradiol.

Another more specific embodiment provides a transdermal delivery system comprising a backing layer affixed to an adhesive polymer matrix, wherein the adhesive polymer matrix comprises: (a) about 0.5% (w/w) to about 10% (w/w) of a first penetration enhancer selected from the group consisting of lactic acid and a pharmaceutically acceptable salt thereof; (b) about 0.5% (w/w) to about 10% (w/w) of a second penetration enhancer selected from the group consisting of glyceryl monooleate and lauryl lactate; (c) an adhesive polymer; (d) a humectant; (e) levonorgestrel; and (f) ethinyl estradiol.

Another more specific embodiment provides a transdermal delivery system comprising a backing layer affixed to an adhesive polymer matrix, wherein the adhesive polymer matrix comprises: (a) about 0.5% (w/w) to about 10% (w/w) of a first penetration enhancer selected from the group consisting of levulinic acid and a pharmaceutically acceptable salt thereof; (b) about 0.5% (w/w) to about 10% (w/w) of a second penetration enhancer selected from the group consisting of glyceryl monooleate and lauryl lactate; (c) an adhesive polymer; (d) a humectant; (e) levonorgestrel; and (f) ethinyl estradiol.

Another more specific embodiment provides a transdermal delivery system comprising an overlay layer affixed to an adhesive polymer matrix, wherein the adhesive polymer matrix comprises: (a) about 0.5% (w/w) to about 10% (w/w) of a first penetration enhancer selected from the group consisting of levulinic acid and a pharmaceutically acceptable salt thereof; (b) about 0.5% (w/w) to about 10% (w/w) of a second penetration enhancer selected from the group consisting of glyceryl monooleate and lauryl lactate; (c) an adhesive polymer; (d) a humectant; (e) levonorgestrel; and (f) ethinyl estradiol.

Another aspect of the invention provides a method of transdermally administering levonorgestrel and ethinyl estradiol to a subject. The method comprises applying a transdermal delivery system described herein to the skin of the subject.

Another aspect of the invention provides a method of controlling fertility in a female subject. The method comprises applying a transdermal delivery system described herein to the skin of the female subject. In certain embodiments, the transdermal delivery system is replaced once each week for at least three successive weeks.

DETAILED DESCRIPTION OF THE INVENTION

Figure 1:
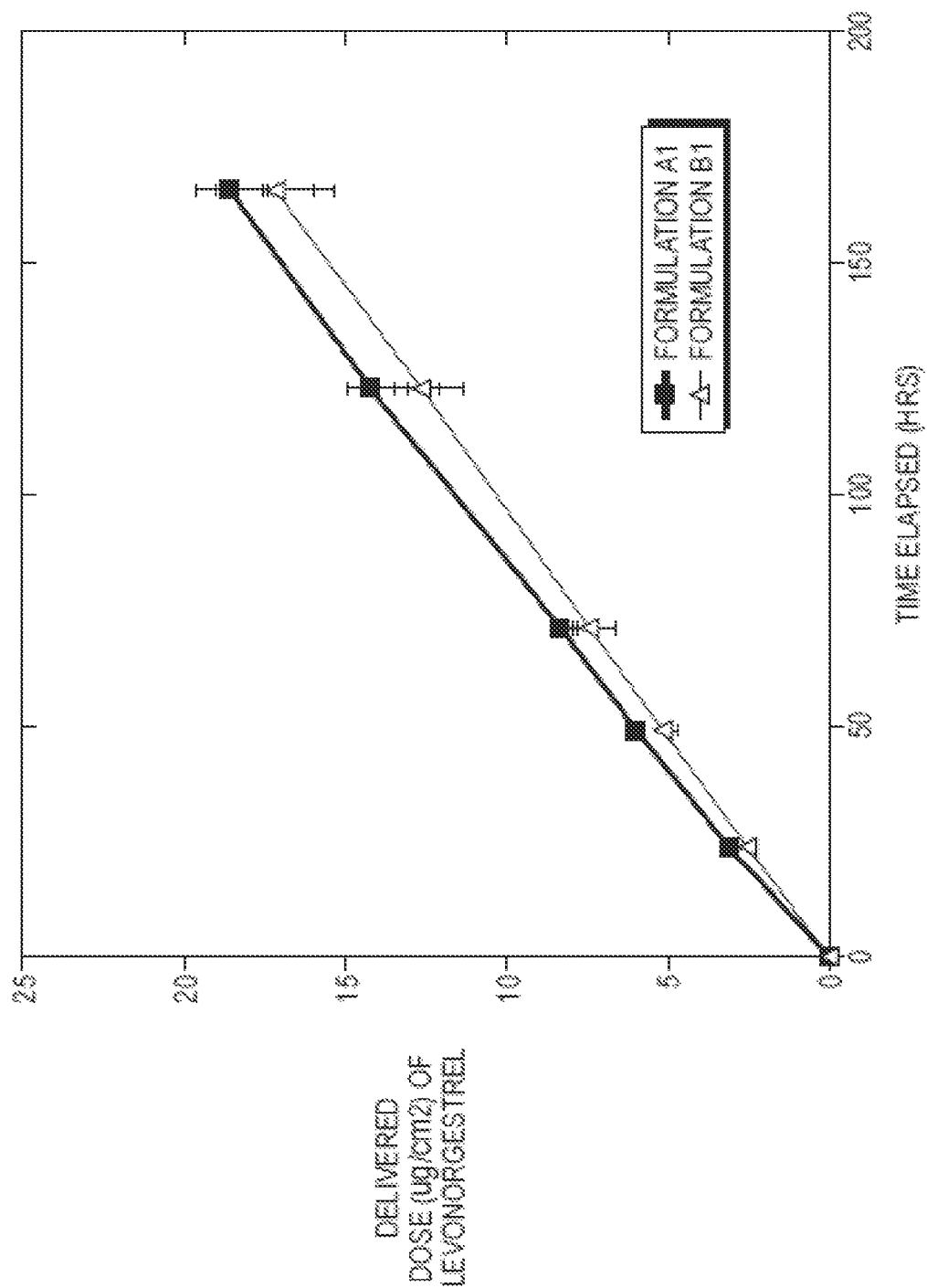
FIG. 1 is a graph showing the delivered dose of levonorgestrel as a function of time in the transdermal flux test described in Example 5.

The invention provides transdermal delivery systems, medical kits, and methods for using the transdermal delivery systems and kits for medical applications, such as delivery of contraceptive agents to control fertility. The transdermal delivery systems utilize a novel combination of agents that increase the skin penetration rate of medicinal agents, such as levonorgestrel and ethinyl estradiol. Various aspects of the invention are set forth below in sections; however, aspects of the invention described in one particular section are not to be limited to any particular section.

I. DEFINITIONS

To facilitate an understanding of the present invention, a number of terms and phrases are defined below.

The terms "a" and "an" as used herein mean "one or more" and include the plural unless the context is inappropriate.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. TRANSDERMAL DELIVERY SYSTEMS

The invention provides transdermal delivery systems for administration of one or more medicinal agents. General features of the transdermal delivery systems are described below, along with specific, exemplary transdermal delivery systems for delivery of contraceptive agents. As a general matter, the transdermal delivery systems contain an adhesive polymer matrix that comprises one or more medicinal agents, an adhesive polymer, and two or three penetration enhancers selected from the group consisting of levulinic acid, glyceryl monooleate, lauryl lactate, isopropyl myristate, lactic acid, and pharmaceutically acceptable salts thereof. The identity and amount of the aforementioned penetration enhancers is selected in order to achieve the desired release properties for the medicinal agent(s) while minimizing the occurrence of adverse events, such as skin irritation caused by the adhesive polymer matrix. One advantage of using the aforementioned penetration enhancers is that certain medicinal agents (such as a combination of levonorgestrel and ethinyl estradiol) can be dissolved in sufficient quantities in the adhesive polymer matrix to provide a medical benefit when the transdermal delivery system is applied to the skin of the patient. In particular, use of the aforementioned penetration enhancers permits preparation of a transdermal delivery system for levonorgestrel and ethinyl estradiol that does not require the use of dimethyl sulfoxide (DMSO), and, accordingly, in certain embodiments, the adhesive polymer matrix of transdermal delivery systems described herein do not contain DMSO. A backing layer and/or an overlay layer may be affixed to a surface of the adhesive polymer matrix. The transdermal delivery systems are useful for the medical applications and medical kits described herein.

General Features of the Transdermal Delivery Systems

A first configuration provides a transdermal delivery system comprising an adhesive polymer matrix affixed to a backing layer or an overlay layer, wherein the adhesive polymer matrix comprises (a) two or three penetration enhancers selected from the group consisting of levulinic acid, glyceryl monooleate, lauryl lactate, isopropyl myristate, lactic acid, and pharmaceutically acceptable salts thereof, (b) an adhesive polymer, and (c) at least one medicinal agent.

A second configuration provides a transdermal delivery system comprising an adhesive polymer matrix affixed to a backing layer or an overlay layer, wherein the adhesive polymer matrix comprises (a) a first penetration enhancer selected from the group consisting of levulinic acid and a pharmaceutically acceptable salt thereof, (b) a second penetration enhancer selected from the group consisting of glyceryl monooleate and lauryl lactate, (c) an adhesive polymer, and (d) at least one medicinal agent.

A third configuration provides a transdermal delivery system comprising an adhesive polymer matrix affixed to a backing layer or an overlay layer, wherein the adhesive polymer matrix comprises (a) a first penetration enhancer selected from the group consisting of lactic acid and a pharmaceutically acceptable salt thereof, (b) a second penetration enhancer selected from the group consisting of glyceryl monooleate and lauryl lactate, (c) an adhesive polymer, and (d) at least one medicinal agent.

A fourth configuration provides a transdermal delivery system comprising an adhesive polymer matrix affixed to a backing layer or an overlay layer, wherein the adhesive polymer matrix comprises (a) a first penetration enhancer selected from the group consisting of lactic acid and a pharmaceutically acceptable salt, (b) a second penetration enhancer selected from the group consisting of levulinic acid and a pharmaceutically acceptable salt thereof, (c) an adhesive polymer, and (d) at least one medicinal agent.

A fifth configuration provides a transdermal delivery system, comprising a backing layer affixed to an adhesive polymer matrix, wherein the adhesive polymer matrix comprises: (a) about 0.5% (w/w) to about 10% (w/w) of a first penetration enhancer selected from the group consisting of levulinic acid and a pharmaceutically acceptable salt thereof; (b) about 0.5% (w/w) to about 10% (w/w) of a second penetration enhancer selected from the group consisting of glyceryl monooleate, lauryl lactate, and isopropyl myristate; (c) an adhesive polymer; and (d) a medicinal agent.

The identity and/or amount of components in the transdermal delivery systems can be adjusted in order to achieve desired performance properties. For example, the identity and amount of the penetration enhancers can be selected in order to achieve the desired release properties for the medicinal agent(s) while minimizing the occurrence of adverse events, such as skin irritation caused by the adhesive polymer matrix. Further description of exemplary components that may be used in the transdermal delivery systems are described below.

Adhesive Polymer Matrix

The adhesive polymer matrix comprises at least two penetration enhancers, an adhesive polymer, a medicinal agent, and optionally a humectant. Exemplary penetration enhancers, adhesive polymers, medicinal agents, and humectants contemplated for use in the transdermal delivery systems are provided below.

A. Penetration Enhancers

The adhesive polymer matrix comprises at least two penetration enhancers selected from the group levulinic acid, glyceryl monooleate, lauryl lactate, isopropyl myristate, lactic acid, and pharmaceutically acceptable salts thereof. The identity and amount of the penetration enhancers may be adjusted in order to achieve particular release properties for the medicinal agent(s) while minimizing the occurrence of adverse events, such as skin irritation caused by the adhesive polymer matrix.

In certain embodiments, the adhesive polymer matrix comprises (a) a first penetration enhancer selected from the group consisting of levulinic acid and a pharmaceutically acceptable salt thereof, and (b) a second penetration enhancer selected from the group consisting of glyceryl monooleate and lauryl lactate. In certain embodiments, the first penetration enhancer is levulinic acid. In certain embodiments, the second penetration enhancer is glyceryl monooleate. In certain other embodiments, the second penetration enhancer is lauryl lactate.

In certain embodiments, the adhesive polymer matrix comprises (a) a first penetration enhancer selected from the group consisting of lactic acid and a pharmaceutically acceptable salt thereof, and (b) a second penetration enhancer selected from the group consisting of glyceryl monooleate and lauryl lactate. In certain embodiments, the first penetration enhancer is lactic acid. In certain embodiments, the second penetration enhancer is glyceryl monooleate.

In certain embodiments, the adhesive polymer matrix comprises (a) a first penetration enhancer selected from the group consisting of lactic acid and a pharmaceutically acceptable salt thereof, and (b) a second penetration enhancer selected from the group consisting of levulinic acid and a pharmaceutically acceptable salt thereof. In certain embodiments, the first penetration enhancer is lactic acid and the second penetration is levulinic acid.

In certain embodiments, the adhesive polymer matrix comprises a third penetration enhancer, such as isopropyl myristate.

The amount of the first penetration enhancer and second penetration enhancer can be selected in order to achieve the desired release properties of a medicinal agent from the adhesive polymer matrix. For example, in certain embodiments, the adhesive polymer matrix may comprise (a) about 0.5% (w/w) to about 10% (w/w) of a first penetration enhancer. In certain other embodiments, the adhesive polymer matrix may comprise from about 2.5% (w/w) to about 5% (w/w) of the first penetration enhancer, or from about 3.0% (w/w) to about 4.0% (w/w) of the first penetration enhancer, such as when the first penetration enhancer is levulinic acid. In certain other embodiments, the adhesive polymer matrix may comprise from about 3% (w/w) to about 5% (w/w) of the first penetration enhancer, or from about 3.5% (w/w) to about 4.0% (w/w) of the first penetration enhancer, such as when the first penetration enhancer is levulinic acid.

In certain embodiments, the adhesive polymer matrix comprises (a) about 0.5% (w/w) to about 10% (w/w) of a second penetration enhancer. In certain other embodiments, the adhesive polymer matrix may comprise from about 2.0% (w/w) to about 4.0% (w/w) of the second penetration enhancer, or from about 2.25% (w/w) to about 3.25% (w/w) of the second penetration enhancer, such as when the second penetration enhancer is glyceryl monooleate. In certain other embodiments, the adhesive polymer matrix may comprise from about 6.0% (w/w) to about 10.0% (w/w) of the second penetration enhancer, or from about 6.5% (w/w) to about 8.5% (w/w) of the second penetration enhancer, such as when the second penetration enhancer is lauryl lactate. In certain other embodiments, the adhesive polymer matrix may comprise from about 2.0% (w/w) to about 3.0% (w/w) of the second penetration enhancer, or from about 2.25% (w/w) to about 2.75% (w/w) of the second penetration enhancer, such as when the second penetration enhancer is glyceryl monooleate. In certain other embodiments, the adhesive polymer matrix may comprise from about 6.0% (w/w) to about 9.0% (w/w) of the second penetration enhancer, or from about 7.0% (w/w) to about 8.0% (w/w) of the second penetration enhancer, such as when the second penetration enhancer is lauryl lactate. In yet other embodiments, the adhesive polymer matrix may comprise from about 7.2% (w/w) to about 7.5% (w/w) of the second penetration enhancer, such as when the second penetration enhancer is lauryl lactate.

The adhesive polymer matrix can be characterized according to the ratio of weight percent of first penetration enhancer to second penetration enhancer in the adhesive polymer matrix. In certain embodiments, the ratio of weight percent of first penetration enhancer to second penetration enhancer in the adhesive polymer matrix is in the range of about 1:1 to 2:1. In certain other embodiments, the ratio of weight percent of first penetration enhancer to second penetration enhancer in the adhesive polymer matrix is about 1.5:1, such as when the first penetration enhancer is levulinic acid and the second penetration enhancer is glyceryl monooleate. In certain other embodiments, the ratio of weight percent of first penetration enhancer to second penetration enhancer in the adhesive polymer matrix is in the range of about 1:1 to 1:3, or about 1:2, such as when the first penetration enhancer is levulinic acid and the second penetration enhancer is lauryl lactate.

In embodiments where the adhesive polymer matrix comprises a third penetration enhancer, the adhesive polymer matrix may comprise from about 0.5% (w/w) to about 15% (w/w) of the third penetration enhancer, such as isopropyl myristate. In certain other embodiments where the adhesive polymer matrix comprises a third penetration enhancer, the adhesive polymer matrix may comprise from about 4% (w/w) to about 10% (w/w) of the third penetration enhancer, such as isopropyl myristate. In certain other embodiments where the adhesive polymer matrix comprises a third penetration enhancer, the adhesive polymer matrix may comprise from about 3% (w/w) to about 8% (w/w) of the third penetration enhancer, such as isopropyl myristate.

B. Adhesive Polymers

Adhesive polymers contemplated for use include, for example, a polyacrylate copolymer, a polyisobutylene copolymer, or a silicone adhesive. Other adhesive polymers contemplated for use in the adhesive polymer matrix include, for example, polyethylene, polypropylene, ethylene/propylene copolymers, ethylene/ethylacrylate copolymers, ethylene/vinyl acetate copolymers, silicone elastomers, polydimethylsiloxanes, neoprene rubber, polyisobutylene, polyacrylates, chlorinated polyethylene, polyvinyl chloride, vinyl chloride-vinyl acetate copolymers, cross-linked polymethacrylate polymers, polyvinylidene chloride, poly(ethylene terephthalate), butyl rubber, epichlorohydrin rubbers, ethylene vinyl alcohol copolymers, ethylene-vinyloxyethanol copolymers, silicone copolymers (such as polysiloxane-polycarbonate copolymers, polysiloxanepolyethylene oxide copolymers, polysiloxane-polymethacrylate copolymers, polysiloxane-alkylene copolymers (e.g., polysiloxane-ethylene/silane copolymers), cellulose polymers (such as methyl or ethyl cellulose, hydroxypropyl methyl cellulose, and cellulose esters), polycarbonates, polytetrafluoroethylene, and combinations thereof.

Desirably, the adhesive polymer has a glass transition temperature less than room temperature. The adhesive polymer may have a degree of crystallinity at room temperature. Cross-linking nonmeric units or sites can be incorporated into such polymers. For example, cross-linking monomers can be incorporated into polyacrylate polymers, which provide sites for cross-linking monomers for polyacrylate polymers that include, for example, polymethacrylic esters of polyols such as butylene diacrylate, dimethacrylate, and trimethylol propane trimethacrylate. Other monomers which provide such sites include, for example, allyl acrylate, allyl methacrylate, and diallyl maleate.

In certain embodiments, the adhesive polymer comprises the diradical represented by the following formula:

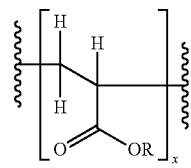

wherein x represents the number of repeating units sufficient to provide the desired properties in the adhesive polymer (such as where x is an integer in the range of about 10 to about 100) and R is H or $C_1$-$C_{10}$ alkyl (such as methyl, ethyl, butyl, 2-ethylhexyl, octyl, and decyl). In certain embodiments, groups attached at the radical position in the above formula are hydrogen atoms.

In certain other embodiments, the adhesive polymer is a polyacrylate adhesive copolymer. In certain embodiments, the adhesive polymer is an acrylate-vinylacetate copolymer. In certain other embodiments, the adhesive polymer is a polyacrylate copolymer comprising a 2-ethylhexyl acrylate monomer and approximately 50-60% (w/w) of vinyl acetate as a co-monomer. One example of a suitable polyacrylate adhesive copolymer for use in the present invention includes, but is not limited to, that sold under the tradename of DURO TAK 87-4098 (an acrylate-vinylacetate copolymer) by National Starch and Chemical Co., Bridgewater, N.J.

In certain embodiments, the adhesive polymer is a polyacrylate copolymer, such as a polyacrylate copolymer comprising a 2-ethylhexyl acrylate monomer. In certain embodiments, the adhesive polymer is a polyacrylate copolymer comprising a $C_6$-$C_{10}$ alkyl acrylate monomer and a vinyl acetate monomer. In yet other embodiments, the adhesive polymer is a random copolymer of 2-ethylhexyl acrylate and vinyl acetate.

The adhesive polymer can be characterized according to its weight average molecular weight. In certain embodiments, the adhesive polymer has a weight average molecular weight of from about 10,000 g/mol to about 50,000 g/mol, about 50,000 g/mol to about 200,000 g/mol, about 200,000 g/mol to about 500,000 g/mol, about 500,000 g/mol to about 1,000,000 g/mol, or about 50,000 g/mol to about 500,000 g/mol. In certain embodiments, the adhesive polymer has a weight average molecular weight greater than 50,000 g/mol.

The amount of adhesive polymer in the adhesive polymer matrix can be selected in order to achieve desired performance properties for the transdermal delivery system, such as particular release properties of a medicinal agent from the adhesive polymer matrix. In certain embodiments, the adhesive polymer matrix comprises at least about 55% (w/w) adhesive polymer. In certain other embodiments, the adhesive polymer matrix comprises from about 80% (w/w) to about 92% (w/w) adhesive polymer. In yet other embodiments, the adhesive polymer matrix comprises from about 86% (w/w) to about 90% (w/w) adhesive polymer. In yet other embodiments, the adhesive polymer matrix comprises from about 88% (w/w) to about 90% (w/w) adhesive polymer.

C. Medicinal Agents

The transdermal delivery system is contemplated to be applicable for delivery a wide array of medicinal agents. The medicinal agents levonorgestrel and ethinyl estradiol are examples of contraceptive agents that can be included in the adhesive polymer matrix. Exemplary other medicinal agents that may be included in the adhesive polymer matrix include, for example, a mono-ester of ethinyl estradiol or a di-ester of ethinyl estradiol. The monoester may be 3-ester or a 17-ester. Exemplary estradiol esters include, for example, estradiol-3,17-diacetate; estradiol-3-acetate; estradiol-17-acetate; estradiol-3,17-divalerate; estradiol-3 valerate; estradiol-17-valerate; 3-pivilate ester; 17-pivilate ester; 3,17-dipivilate ester; 3-propionate ester; 17-propionate ester; 3,17-dipropionate ester; 3-cyclopentyl-propionate ester; 17-cyclopentyl-propionate ester; 3,17-di-cyclopentyl-propionate ester; and corresponding cypionate esters, heptanoate esters, and benzoate esters. The medicinal agent may also be a progestin, such norgestrel, norgestimate, desogestrel, gestodene, norethindrone, nore-thynodrel, hydrogesterone, ethynodiol dicetate, hydroxyprogesterone caproate, medroxyprogesterone acetate, norethindrone acetate, progesterone, megestrol acetate, or gestogen.

The amount of the medicinal agent(s) in the adhesive polymer matrix may be selected according to the solubility of the therapeutic agent, the desired daily dosage of medicinal agent to be administered, the total amount of medicinal agent to be administered to the subject while the transdermal delivery system is affixed to the subject (often a period of several days), and other factors. In certain embodiments where the adhesive polymer matrix comprises levonorgestrel, the adhesive polymer matrix may comprise from about 0.6% (w/w) to about 1.0% (w/w) levonorgestrel. In certain other embodiments where the adhesive polymer matrix comprises levonorgestrel, the adhesive polymer matrix may comprise from about 0.7% (w/w) to about 0.9% (w/w) levonorgestrel. In certain other embodiments where the adhesive polymer matrix comprises levonorgestrel, the adhesive polymer matrix may comprise from about 0.75% (w/w) to about 0.85% (w/w) levonorgestrel. In certain embodiments where the adhesive polymer matrix comprises ethinyl estradiol, the adhesive polymer matrix may comprise from about 0.6% (w/w) to about 1.0% (w/w) ethinyl estradiol. In certain embodiments where the adhesive polymer matrix comprises ethinyl estradiol, the adhesive polymer matrix may comprise from about 0.7% (w/w) to about 0.9% (w/w) ethinyl estradiol. In certain embodiments where the adhesive polymer matrix comprises ethinyl estradiol, the adhesive polymer matrix may comprise from about 0.8% (w/w) to about 0.9% (w/w) ethinyl estradiol.

D. Humectant

Humectants contemplated for use include, for example, materials comprising a polyvinylpyrrolidone copolymer. Other humectants contemplated for use in the adhesive polymer matrix include, for example, polyvinylpyrrolidone. In certain other embodiments, the humectant comprises a copolymer of vinylpyrrolidone and vinyl acetate. In yet other embodiments, the humectant is a copolymer of vinylpyrrolidone and vinyl acetate, said copolymer having a weight average molecular weight of about 30,000 g/mol to about 50,000 g/mol. In still other embodiments, the humectant is a copolymer of vinylpyrrolidone and vinyl acetate, said copolymer having a weight average molecular weight of about 40,000 g/mol. In certain embodiments, the copolymer of vinylpyrrolidone and vinyl acetate comprises (i) from about 55% (w/w) to about 65% (w/w) vinylpyrrolidone and (ii) from about 35% (w/w) to about 45% (w/w) vinyl acetate. In certain embodiments, the copolymer of vinylpyrrolidone and vinyl acetate comprises about 60% (w/w) vinylpyrrolidone and about 40% (w/w) vinyl acetate. Additional humectants that may be used include propylene glycol and dipropylene glycol.

The amount of humectant in the adhesive polymer matrix can be selected in order to achieve desired performance properties for the transdermal delivery system. In certain embodiments, the adhesive polymer matrix comprises less than about 15% (w/w) humectant. In certain other embodiments, the adhesive polymer matrix comprises less than about 10% (w/w) humectant. In certain other embodiments, the adhesive polymer matrix comprises from about 2% (w/w) to about 8% (w/w) humectant. In certain other embodiments, the adhesive polymer matrix comprises from about 2.5% (w/w) to about 3.5% (w/w) humectant. In certain other embodiments, the adhesive polymer matrix comprises from about 2.5% (w/w) to about 4% (w/w) humectant. In certain other embodiments, the adhesive polymer matrix comprises from about 2.75% (w/w) to about 3.75% (w/w) humectant. In certain other embodiments, the adhesive polymer matrix comprises from about 2.5% (w/w) to about 3.5% (w/w) humectant.

In certain embodiments, the adhesive polymer matrix may comprise more than one humectant. In certain embodiments, the adhesive polymer matrix comprises two humectants, such as where the first humectant is a polyvinylpyrrolidone copolymer (e.g., a copolymer of vinylpyrrolidone and vinyl acetate comprising (i) from about 55% (w/w) to about 65% (w/w) vinylpyrrolidone and (ii) from about 35% (w/w) to about 45% (w/w) vinyl acetate), and the second humectant is propylene glycol or dipropylene glycol. In certain embodiments, the adhesive polymer matrix may comprises from about 2.5% (w/w) to about 3.5% (w/w) of the first humectant, and about 2% (w/w) to about 10% (w/w) (or about 2% (w/w) to about 8% (w/w)) of the second humectant. In yet other embodiments, the adhesive polymer matrix comprises from about 0.1% (w/w) to about 10% (w/w) of propylene glycol or dipropylene glycol.

E. Physical Features of Adhesive Polymer Matrix

The adhesive polymer matrix can be characterized according to its physical features, such as size and/or release properties of a medicinal agent. Accordingly, in certain embodiments, the transdermal delivery system is characterized by comprising an adhesive polymer matrix having a thickness of about 50 μm to about 150 μm. In certain other embodiments, the adhesive polymer matrix has a thickness of about 110 μm to about 140 μm. In certain other embodiments, the adhesive polymer matrix has a thickness of about 100 μm. In yet other embodiments, the surface of the adhesive polymer matrix opposite the backing layer has a surface area of about 15 cm². In yet other embodiments, the surface of the adhesive polymer matrix opposite the backing layer has a surface area of from about 10 cm² to about 15 cm², or about 10 cm² to about 20 cm².

The transdermal delivery system can be characterized according to the rate at which a medicinal agent is released from the transdermal delivery device. For example, in embodiments where the adhesive polymer matrix comprises ethinyl estradiol and levonorgestrel, the transdermal delivery system may be characterized by having an adhesive polymer matrix formulated for delivery of ethinyl estradiol and levonorgestrel where the ethinyl estradiol is transdermally delivered at a rate of from about 5 μg to about 25 μg per day for a term of about seven days, and the levonorgestrel is transdermally delivered at a rate of about 25 μg to about 35 μg per day for a term of about seven days. In certain other embodiments, the adhesive polymer matrix is formulated for delivery of ethinyl estradiol and levonorgestrel where the ethinyl estradiol is transdermally delivered at a rate of from about 10 μg to about 20 μg per day for a term of about seven days, and the levonorgestrel is transdermally delivered at a rate of about 30 μg per day for a term of about seven days.

The transdermal delivery system can also be characterized according to a subject's serum concentration of a medicinal agent released from the transdermal delivery system to the subject. For example, in embodiments where the adhesive polymer matrix comprises levonorgestrel, the transdermal delivery system may be characterized by producing a serum concentration of levonorgestrel of at least 1,000 pg/mL in a human subject.

Backing Layer

The backing layer, when present, is affixed to the adhesive polymer matrix. The backing layer provides support and protection of the adhesive polymer matrix. Desirably, the backing layer is flexible so that it can be brought into close contact with a desired topical location on a subject. Desirably, the backing layer is fabricated from a material that does not absorb medicinal agent(s) in the adhesive polymer matrix, and the backing layer desirably does not allow medicinal agent(s) in the adhesive polymer matrix to be released from the side of the support affixed to the backing layer.

The size of the backing layer can be substantially the same size layer as the adhesive polymer matrix, or it can have a larger size in order to extend beyond the side(s) of the adhesive polymer matrix, such as extending outwardly beyond the adhesive polymer transdermal delivery system to the skin of a subject.

The backing layer may be made of, for example, non-woven fabrics, woven fabrics, films (including sheets), porous bodies, foamed bodies, paper, composite materials obtained by laminating a film on a non-woven fabric or fabric, or a combination of the foregoing. When the transdermal delivery system is to be applied to the skin of a subject for several days (e.g., 5, 7, or 9 days), there can be benefits to using a backing layer made of a microporous and/or breathable laminate, so that hydration or maceration of the skin is minimized.

Exemplary non-woven fabrics that may be used include, for example, polyolefin resins such as polyethylene and polypropylene; polyester resins such as polyethylene terephthalate, polybutylene terephthalate and polyethylene naphthalate; rayon; polyamide; poly(ester ether); polyurethane; polyacrylic resins; polyvinyl alcohol; styrene-isoprene-styrene copolymers; styrene-ethylene-propylene-styrene copolymers; and combinations thereof. Exemplary fabrics that may be used in the backing layer include, for example, cotton, rayon, polyacrylic resins, polyester resins, polyvinyl alcohol, and combinations thereof.

Exemplary films that may be used in the backing layer include, for example, polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; polyvinyl alcohol; ethylene-vinyl alcohol copolymers; polyvinyl chloride; polystyrene; polyurethane; polyacrylonitrile; fluororesins; styrene-isoprene-styrene copolymers; styrene-butadiene rubber; polybutadiene; ethylene-vinyl acetate copolymers; polyamide; polysulfone; and combinations thereof. Exemplary paper that may be used in the backing layer includes, for example, may include, impregnated paper, coated paper, wood free paper, Kraft paper, Japanese paper, glassine paper, synthetic paper, and combinations thereof.

In certain embodiments, the backing layer comprises a film of high-density and/or low-density polyethylene, polypropylene, polyurethane, polyvinylchloride, polyester (such as poly(ethylene phthalate)), a metal foil (e.g., aluminum foil), or a metal foil laminate of a polymer film.

In certain other embodiments, the backing layer is a laminate comprising a polyester film and an ethylene vinyl acetate copolymer film.

Overlay Layer

The transdermal delivery system may optionally comprise an overlay layer. Numerous overlay layers are known in the art and are amenable for use in the present invention. The overlay layer contains adhesive on one surface of the layer, said surface with the adhesive being applied over the adhesive polymer matrix and, if present, the backing layer, and extending beyond the adhesive polymer matrix (and, if present, the backing layer) in order to improve adhesion of the transdermal delivery system to the skin of a patient.

In one configuration, the overlay layer extends beyond the perimeter of the adhesive polymer matrix (and backing layer, if present) in all directions, such as by a margin of about 0.1 to about 2.5 cm, 0.1 to about 1.0 cm, about 0.3 to about 0.7 cm, or 0.5 cm. In a different configuration, the overlay layer extends partially beyond the edge of the adhesive polymer matrix (and backing layer, if present) in certain directions forming "tabs" of overlay material. The overlay layer may be fabricated with other components of the transdermal delivery system (where it may be affixed to the backing layer during fabrication of the transdermal delivery system). Alternatively, the overlay layer may be fabricated separately, e.g., with its own releasable liner, in a separate pouch, such that the overlay may be applied at the discretion of the user.

Release Liner

The transdermal delivery system may optionally comprise a release liner. The release liner, when present, is temporarily affixed to the surface of the adhesive polymer matrix opposite the backing layer (or overlay layer). The release liner protects the adhesive polymer matrix prior to application of the adhesive polymer layer to the skin of a patient. Specifically, the release liner is separated from the adhesive polymer matrix just prior to application of the adhesive polymer matrix to the skin of a patient.

Numerous release liners are described in the art and are contemplated to be amenable for use in the present invention. Exemplary release liners include, for example, polyethylene-coated wood free paper, polyolefin-coated glassine paper, a polyethylene terephthalate (polyester) film, a polypropylene film, or the like with a silicone treatment. Desirably, the release liner is fabricated from a material that does not absorb medicinal agent(s) in the release liner.

Exemplary Transdermal Delivery Systems Containing Levulinic Acid or a Pharmaceutically Acceptable Salt Thereof One aspect of the invention provides a transdermal delivery system, comprising a backing layer affixed to an adhesive polymer matrix, wherein the adhesive polymer matrix comprises:

a. about 0.5% (w/w) to about 10% (w/w) of a first penetration enhancer selected from the group consisting of levulinic acid and a pharmaceutically acceptable salt thereof;

b. about 0.5% (w/w) to about 10% (w/w) of a second penetration enhancer selected from the group consisting of glyceryl monooleate and lauryl lactate;
c. an adhesive polymer;
d. a humectant;
e. levonorgestrel; and
f. ethinyl estradiol.

In certain embodiments, the first penetration enhancer is levulinic acid. In certain embodiments, the second penetration enhancer is glyceryl monooleate. In certain other embodiments, the second penetration enhancer is lauryl lactate.

The amount of first and second penetration enhancers can be selected in order to achieve desired performance properties. In certain embodiments, the adhesive polymer matrix comprises from about 3% (w/w) to about 5% (w/w) of the first penetration enhancer. In certain other embodiments, the adhesive polymer matrix comprises from about 3.5% (w/w) to about 4.0% (w/w) of the first penetration enhancer, such as when the first penetration enhancer is levulinic acid. In certain embodiments, the adhesive polymer matrix comprises from about 2.0% (w/w) to about 3.0% (w/w) of the second penetration enhancer. In certain embodiments, the adhesive polymer matrix comprises from about 2.25% (w/w) to about 2.75% (w/w) of the second penetration enhancer, such as when the second penetration enhancer is glyceryl monooleate. In certain other embodiments, the adhesive polymer matrix may comprise from about 6.0% (w/w) to about 9.0% (w/w) of the second penetration enhancer, or from about 7.0% (w/w) to about 8.0% (w/w) of the second penetration enhancer, such as when the second penetration enhancer is lauryl lactate. In certain other embodiments, the adhesive polymer matrix comprises from about 2.5% (w/w) to about 5% (w/w) of the first penetration enhancer. In certain other embodiments, the adhesive polymer matrix comprises from about 3.0% (w/w) to about 4.0% (w/w) of the first penetration enhancer, such as when the first penetration enhancer is levulinic acid. In certain embodiments, the adhesive polymer matrix comprises from about 2.0% (w/w) to about 4.0% (w/w) of the second penetration enhancer. In certain embodiments, the adhesive polymer matrix comprises from about 2.25% (w/w) to about 3.25% (w/w) of the second penetration enhancer, such as when the second penetration enhancer is glyceryl monooleate. In certain other embodiments, the adhesive polymer matrix may comprise from about 6.0% (w/w) to about 10.0% (w/w) of the second penetration enhancer, from about 6.5% (w/w) to about 8.5% (w/w) of the second penetration enhancer, or from about 7.2% (w/w) to about 7.5% (w/w) of the second penetration enhancer, such as when the second penetration enhancer is lauryl lactate.

In certain embodiments, the ratio of weight percent of first penetration enhancer to second penetration enhancer in the adhesive polymer matrix is in the range of about 1:1 to 2:1. In certain other embodiments, the ratio of weight percent of first penetration enhancer to second penetration enhancer in the adhesive polymer matrix is about 1.5:1, such as when the first penetration enhancer is levulinic acid and the second penetration enhancer is glyceryl monooleate. In certain other embodiments, the ratio of weight percent of first penetration enhancer to second penetration enhancer in the adhesive polymer matrix is in the range of about 1:1 to 1:3, or about 1:2, such as when the first penetration enhancer is levulinic acid and the second penetration enhancer is lauryl lactate.

In certain embodiments, the adhesive polymer matrix further comprises from about 0.5% (w/w) to about 15% (w/w) of isopropyl myristate. In certain other embodiments, the adhesive polymer matrix further comprises from about 3% (w/w) to about 8% (w/w) of isopropyl myristate. In certain other embodiments, the adhesive polymer matrix further comprises from about 4% (w/w) to about 10% (w/w) of isopropyl myristate.

The adhesive polymer may be polyacrylate copolymer, a polyisobutylene copolymer, or a silicone adhesive. In certain embodiments, the adhesive polymer is a polyacrylate copolymer. In certain embodiments, the adhesive polymer is an acrylate-vinylacetate copolymer. In certain other embodiments, adhesive polymer is a polyacrylate copolymer comprising a 2-ethylhexyl acrylate monomer. In certain embodiments, the adhesive polymer is a polyacrylate copolymer comprising a $C_6$-$C_{10}$ alkyl acrylate monomer and a vinyl acetate monomer. In certain embodiments, the adhesive polymer is a random copolymer of 2-ethylhexyl acrylate and vinyl acetate.

The amount of adhesive polymer in the adhesive polymer matrix can be adjusted to achieve desired performance characteristics. In certain embodiments, the adhesive polymer matrix comprises at least about 55% (w/w) adhesive polymer. In certain other embodiments, the adhesive polymer matrix comprises from about 80% (w/w) to about 92% (w/w) adhesive polymer. In yet other embodiments, the adhesive polymer matrix comprises from about 86% (w/w) to about 90% (w/w) adhesive polymer. In yet other embodiments, the adhesive polymer matrix comprises from about 88% (w/w) to about 90% (w/w) adhesive polymer.

In certain embodiments, the humectant comprises a polyvinylpyrrolidone copolymer. In certain embodiments, the humectant comprises a copolymer of vinylpyrrolidone and vinyl acetate. In certain embodiments, the humectant is a copolymer of vinylpyrrolidone and vinyl acetate, said copolymer having a weight average molecular weight of about 30,000 g/mol to about 50,000 g/mol. In certain embodiments, the humectant is a copolymer of vinylpyrrolidone and vinyl acetate, said copolymer having a weight average molecular weight of about 40,000 g/mol. In certain embodiments, the copolymer of vinylpyrrolidone and vinyl acetate comprises (i) from about 55% (w/w) to about 65% (w/w) vinylpyrrolidone and (ii) from about 35% (w/w) to about 45% (w/w) vinyl acetate. In certain embodiments, the copolymer of vinylpyrrolidone and vinyl acetate comprises about 60% (w/w) vinylpyrrolidone and about 40% (w/w) vinyl acetate. In certain other embodiments, the copolymer of vinylpyrrolidone and vinyl acetate comprises about 60% (w/w) vinylpyrrolidone, about 40% (w/w) vinyl acetate, and has a weight average molecular weight of about 30,000 g/mol to about 50,000 g/mol.

The amount of humectant can be adjusted to achieved desired performance characteristics. In certain embodiments, the adhesive polymer matrix comprises from about 2% (w/w) to about 8% (w/w) humectant. In certain other embodiments, the adhesive polymer matrix comprises from about 2.5% (w/w) to about 3.5% (w/w) humectant. In certain other embodiments, the adhesive polymer matrix comprises from about 2.5% (w/w) to about 3.75% (w/w) humectant.

The amount of levonorgestrel and ethinyl estradiol can be adjusted to achieve desired performance characteristics. In certain embodiments, the adhesive polymer matrix comprises from about 0.6% (w/w) to about 1.0% (w/w) levonorgestrel. In certain other embodiments, the adhesive polymer matrix comprises from about 0.7% (w/w) to about 0.9% (w/w) levonorgestrel, or about 0.80% (w/w) levonorgestrel. In certain embodiments, the adhesive polymer matrix comprises from about 0.6% (w/w) to about 1.0% (w/w) ethinyl estradiol. In certain other embodiments, the adhesive polymer matrix comprises from about 0.7% (w/w) to about 0.9% (w/w) ethinyl estradiol, or about 0.84% (w/w) ethinyl estradiol.

Another aspect of the invention provides a transdermal delivery system, comprising a backing layer affixed to an adhesive polymer matrix, wherein the adhesive polymer matrix comprises:
 a. about 3.5% (w/w) to about 4% (w/w) of a first penetration enhancer selected from the group consisting of levulinic acid and a pharmaceutically acceptable salt thereof;
 b. about 2.2% (w/w) to about 2.8% (w/w) of a second penetration enhancer that is glyceryl monooleate;
 c. about 86% (w/w) to about 90% (w/w) of an adhesive polymer that is an acrylate-vinylacetate copolymer;
 d. about 2% (w/w) to about 4% (w/w) of a humectant that is a copolymer of vinylpyrrolidone and vinyl acetate;
 e. about 0.7% (w/w) to about 0.9% (w/w) levonorgestrel; and
 f. about 0.7% (w/w) to about 0.9% (w/w) ethinyl estradiol.

In certain embodiments, the adhesive polymer matrix further comprises from about 3% (w/w) to about 8% (w/w) of isopropyl myristate.

Another aspect of the invention provides a transdermal delivery system, comprising a backing layer affixed to an adhesive polymer matrix, wherein the adhesive polymer matrix comprises:
 a. about 3.0% (w/w) to about 4% (w/w) of a first penetration enhancer selected from the group consisting of levulinic acid and a pharmaceutically acceptable salt thereof;
 b. about 2.25% (w/w) to about 3.25% (w/w) of a second penetration enhancer that is glyceryl monooleate;
 c. about 86% (w/w) to about 90% (w/w) of an adhesive polymer that is an acrylate-vinylacetate copolymer;
 d. about 2% (w/w) to about 4% (w/w) of a humectant that is a copolymer of vinylpyrrolidone and vinyl acetate;
 e. about 0.7% (w/w) to about 0.9% (w/w) levonorgestrel; and
 f. about 0.7% (w/w) to about 0.9% (w/w) ethinyl estradiol.

In certain embodiments, the adhesive polymer matrix further comprises from about 4% (w/w) to about 10% (w/w) of isopropyl myristate.

Another aspect of the invention provides a transdermal delivery system, comprising a backing layer affixed to an adhesive polymer matrix, wherein the adhesive polymer matrix comprises:
 a. about 3.5% (w/w) to about 4% (w/w) of a first penetration enhancer selected from the group consisting of levulinic acid and a pharmaceutically acceptable salt thereof;
 b. about 2.2% (w/w) to about 2.8% (w/w) of a second penetration enhancer that is glyceryl monooleate;
 c. about 86% (w/w) to about 90% (w/w) of an adhesive polymer that is a random copolymer of 2-ethylhexyl acrylate and vinyl acetate;
 d. about 2% (w/w) to about 4% (w/w) of a humectant that is a copolymer of vinylpyrrolidone and vinyl acetate;
 e. about 0.7% (w/w) to about 0.9% (w/w) levonorgestrel; and
 f. about 0.7% (w/w) to about 0.9% (w/w) ethinyl estradiol.

In certain embodiments, the adhesive polymer matrix further comprises from about 3% (w/w) to about 8% (w/w) of isopropyl myristate.

Another aspect of the invention provides a transdermal delivery system, comprising a backing layer affixed to an adhesive polymer matrix, wherein the adhesive polymer matrix comprises:
 a. about 3.0% (w/w) to about 4% (w/w) of a first penetration enhancer selected from the group consisting of levulinic acid and a pharmaceutically acceptable salt thereof;
 b. about 2.25% (w/w) to about 3.25% (w/w) of a second penetration enhancer that is glyceryl monooleate;
 c. about 86% (w/w) to about 90% (w/w) of an adhesive polymer that is a random copolymer of 2-ethylhexyl acrylate and vinyl acetate;
 d. about 2% (w/w) to about 4% (w/w) of a humectant that is a copolymer of vinylpyrrolidone and vinyl acetate;
 e. about 0.7% (w/w) to about 0.9% (w/w) levonorgestrel; and
 f. about 0.7% (w/w) to about 0.9% (w/w) ethinyl estradiol.

In certain embodiments, the adhesive polymer matrix further comprises from about 4% (w/w) to about 10% (w/w) of isopropyl myristate.

Another aspect of the invention provides a transdermal delivery system, comprising a backing layer affixed to an adhesive polymer matrix, wherein the adhesive polymer matrix comprises:
 a. about 3.5% (w/w) to about 4% (w/w) levulinic acid;
 b. about 2.2% (w/w) to about 2.8% (w/w) glyceryl monooleate;
 c. about 86% (w/w) to about 90% (w/w) of an adhesive polymer that is an acrylate-vinylacetate copolymer;
 d. about 2% (w/w) to about 4% (w/w) of a humectant that is a copolymer of vinylpyrrolidone and vinyl acetate;
 e. about 0.7% (w/w) to about 0.9% (w/w) levonorgestrel; and
 f. about 0.7% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
 a. about 3.0% (w/w) to about 4% (w/w) levulinic acid;
 b. about 2.25% (w/w) to about 3.25% (w/w) glyceryl monooleate;
 c. about 86% (w/w) to about 90% (w/w) of an adhesive polymer that is an acrylate-vinylacetate copolymer;
 d. about 2% (w/w) to about 4% (w/w) of a humectant that is a copolymer of vinylpyrrolidone and vinyl acetate;
 e. about 0.7% (w/w) to about 0.9% (w/w) levonorgestrel; and
 f. about 0.7% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
 a. about 3.5% (w/w) to about 4% (w/w) levulinic acid;
 b. about 2.2% (w/w) to about 2.8% (w/w) glyceryl monooleate;
 c. about 86% (w/w) to about 90% (w/w) of an adhesive polymer that is a random copolymer of 2-ethylhexyl acrylate and vinyl acetate;
 d. about 2% (w/w) to about 4% (w/w) of a humectant that is a copolymer of vinylpyrrolidone and vinyl acetate;
 e. about 0.7% (w/w) to about 0.9% (w/w) levonorgestrel; and
 f. about 0.7% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
 a. about 3.0% (w/w) to about 4% (w/w) levulinic acid;
 b. about 2.25% (w/w) to about 3.25% (w/w) glyceryl monooleate;
 c. about 86% (w/w) to about 90% (w/w) of an adhesive polymer that is a random copolymer of 2-ethylhexyl acrylate and vinyl acetate;
 d. about 2% (w/w) to about 4% (w/w) of a humectant that is a copolymer of vinylpyrrolidone and vinyl acetate;
 e. about 0.7% (w/w) to about 0.9% (w/w) levonorgestrel; and
 f. about 0.7% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
 a. about 3.5% (w/w) to about 3.7% (w/w) levulinic acid;
 b. about 2.2% (w/w) to about 2.4% (w/w) glyceryl monooleate;
 c. about 86% (w/w) to about 90% (w/w) of an adhesive polymer that is a random copolymer of 2-ethylhexyl acrylate and vinyl acetate;
 d. about 2% (w/w) to about 4% (w/w) of a humectant that is a copolymer of vinylpyrrolidone and vinyl acetate;
 e. about 0.8% (w/w) to about 0.9% (w/w) levonorgestrel; and
 f. about 0.8% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
 a. about 3.75% (w/w) levulinic acid;
 b. about 2.5% (w/w) glyceryl monooleate;
 c. about 89% (w/w) of an adhesive polymer that is a random copolymer of 2-ethylhexyl acrylate and vinyl acetate;
 d. about 3.1% (w/w) of a humectant that is a copolymer of vinylpyrrolidone and vinyl acetate;
 e. about 0.80% (w/w) levonorgestrel; and
 f. about 0.84% (w/w) ethinyl estradiol.

Another aspect of the invention provides a transdermal delivery system, comprising a backing layer affixed to an adhesive polymer matrix, wherein the adhesive polymer matrix comprises:
 a. about 3.6% (w/w) levulinic acid;
 b. about 2.3% (w/w) to glyceryl monooleate;
 c. about 84% (w/w) to about 92% (w/w) of an adhesive polymer that is a random copolymer of 2-ethylhexyl acrylate and vinyl acetate;
 d. about 2% (w/w) to about 4% (w/w) of a copolymer of vinylpyrrolidone and vinyl acetate;
 e. about 0.8% levonorgestrel; and
 f. about 0.9% (w/w) ethinyl estradiol.

Another aspect of the invention provides a transdermal delivery system, comprising a backing layer affixed to an adhesive polymer matrix, wherein the adhesive polymer matrix comprises:
 a. about 3.6% (w/w) levulinic acid;
 b. about 2.3% (w/w) to glyceryl monooleate;

c. about 86% (w/w) to about 90% (w/w) of an adhesive polymer that is a random copolymer of 2-ethylhexyl acrylate and vinyl acetate;
d. about 2% (w/w) to about 4% (w/w) of a copolymer of vinylpyrrolidone and vinyl acetate;
e. about 0.8% levonorgestrel; and
f. about 0.9% (w/w) ethinyl estradiol.

Another aspect of the invention provides a transdermal delivery system, comprising a backing layer affixed to an adhesive polymer matrix, wherein the adhesive polymer matrix comprises:
a. about 3.6% (w/w) levulinic acid;
b. about 2.3% (w/w) to glyceryl monooleate;
c. about 89% (w/w) of an adhesive polymer that is a random copolymer of 2-ethylhexyl acrylate and vinyl acetate;
d. about 3% (w/w) of a copolymer of vinylpyrrolidone and vinyl acetate;
e. about 0.8% levonorgestrel; and
f. about 0.9% (w/w) ethinyl estradiol.

Another aspect of the invention provides a transdermal delivery system, comprising a backing layer affixed to an adhesive polymer matrix, wherein the adhesive polymer matrix comprises:
a. about 3.5% (w/w) to about 4% (w/w) levulinic acid;
b. about 6% (w/w) to about 9% (w/w) lauryl lactate;
c. about 80% (w/w) to about 88% (w/w) of an adhesive polymer that is an acrylate-vinylacetate copolymer;
d. about 2% (w/w) to about 4% (w/w) of a humectant that is a copolymer of vinylpyrrolidone and vinyl acetate;
e. about 0.7% (w/w) to about 0.9% (w/w) levonorgestrel; and
f. about 0.7% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
a. about 3.0% (w/w) to about 4% (w/w) levulinic acid;
b. about 6% (w/w) to about 10% (w/w) lauryl lactate;
c. about 80% (w/w) to about 88% (w/w) of an adhesive polymer that is an acrylate-vinylacetate copolymer;
d. about 2% (w/w) to about 4% (w/w) of a humectant that is a copolymer of vinylpyrrolidone and vinyl acetate;
e. about 0.7% (w/w) to about 0.9% (w/w) levonorgestrel; and
f. about 0.7% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
a. about 3.5% (w/w) to about 4% (w/w) levulinic acid;
b. about 6% (w/w) to about 9% (w/w) lauryl lactate;
c. about 80% (w/w) to about 88% (w/w) of an adhesive polymer that is a random copolymer of 2-ethylhexyl acrylate and vinyl acetate;
d. about 2% (w/w) to about 4% (w/w) of a humectant that is a copolymer of vinylpyrrolidone and vinyl acetate;
e. about 0.7% (w/w) to about 0.9% (w/w) levonorgestrel; and
f. about 0.7% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
a. about 3.0% (w/w) to about 4% (w/w) levulinic acid;
b. about 6% (w/w) to about 10% (w/w) lauryl lactate;
c. about 80% (w/w) to about 88% (w/w) of an adhesive polymer that is a random copolymer of 2-ethylhexyl acrylate and vinyl acetate;
d. about 2% (w/w) to about 4% (w/w) of a humectant that is a copolymer of vinylpyrrolidone and vinyl acetate;
e. about 0.7% (w/w) to about 0.9% (w/w) levonorgestrel; and
f. about 0.7% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
a. about 3.75% (w/w) levulinic acid;
b. about 7.5% (w/w) lauryl lactate;
c. about 84% (w/w) of an adhesive polymer that is a random copolymer of 2-ethylhexyl acrylate and vinyl acetate;
d. about 3.1% (w/w) of a humectant that is a copolymer of vinylpyrrolidone and vinyl acetate;
e. about 0.80% (w/w) levonorgestrel; and
f. about 0.84% (w/w) ethinyl estradiol.

Another aspect of the invention provides a transdermal delivery system, comprising a backing layer affixed to an adhesive polymer matrix, wherein the adhesive polymer matrix comprises:
a. about 3.2% (w/w) to about 3.7% (w/w) levulinic acid;
b. about 6% (w/w) to about 9% (w/w) lauryl lactate;
c. about 80% (w/w) to about 88% (w/w) of an adhesive polymer that is an acrylate-vinylacetate copolymer;
d. about 2% (w/w) to about 4% (w/w) of a humectant that is a copolymer of vinylpyrrolidone and vinyl acetate;
e. about 0.7% (w/w) to about 0.9% (w/w) levonorgestrel; and
f. about 0.7% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
a. about 3.4% (w/w) to about 3.6% (w/w) levulinic acid;
b. about 7% (w/w) to about 8% (w/w) lauryl lactate;
c. about 80% (w/w) to about 88% (w/w) of an adhesive polymer that is an acrylate-vinylacetate copolymer;
d. about 2% (w/w) to about 4% (w/w) of a humectant that is a copolymer of vinylpyrrolidone and vinyl acetate;
e. about 0.7% (w/w) to about 0.8% (w/w) levonorgestrel; and
f. about 0.8% (w/w) to about 0.9% (w/w) ethinyl estradiol.

Another aspect of the invention provides a transdermal delivery system, comprising a backing layer affixed to an adhesive polymer matrix, wherein the adhesive polymer matrix comprises:
a. about 3.5% (w/w) levulinic acid;
b. about 7% (w/w) lauryl lactate;
c. about 80% (w/w) to about 88% (w/w) of an adhesive polymer that is an acrylate-vinylacetate copolymer;
d. about 2% (w/w) to about 4% (w/w) of a humectant that is a copolymer of vinylpyrrolidone and vinyl acetate;
e. about 0.8% (w/w) levonorgestrel; and
f. about 0.8% (w/w) ethinyl estradiol.

Another aspect of the invention provides a transdermal delivery system, comprising a backing layer affixed to an adhesive polymer matrix, wherein the adhesive polymer matrix comprises:
a. about 3.5% (w/w) levulinic acid;
b. about 7% (w/w) lauryl lactate;
c. about 84% (w/w) of an adhesive polymer that is an acrylate-vinylacetate copolymer;
d. about 3% (w/w) of a humectant that is a copolymer of vinylpyrrolidone and vinyl acetate;
e. about 0.8% (w/w) levonorgestrel; and
f. about 0.8% (w/w) ethinyl estradiol.

As described in the general features of transdermal delivery systems, the transdermal delivery system can be characterized according to the rate at which a medicinal agent is released from the system. Accordingly, in certain embodiments, the transdermal delivery system is formulated for delivery of ethinyl estradiol and levonorgestrel, wherein the ethinyl estradiol is transdermally delivered at a rate of from about 5 µg to about 25 µg per day for a term of about seven days, and the levonorgestrel is transdermally delivered at a rate of about 25 µg to about 35 µg per day for a term of about seven days. In certain other embodiments, the transdermal delivery system is formulated for delivery of ethinyl estradiol and levonorgestrel, wherein the ethinyl estradiol is transdermally delivered at a rate of from about 10 µg to about 20 µg per day for a term of about seven days, and the levonorgestrel is transdermally delivered at a rate of about 30 µg per day for a term of about seven days. In yet other embodiments, the transdermal delivery system is characterized by levonorgestrel being transdermally delivered in an amount sufficient to produce a serum concentration of at least 1,000 pg/mL in a human.

In certain embodiments, the adhesive polymer matrix has a thickness of about 50 µm to about 150 µm. In certain other embodiments, the adhesive polymer matrix has a thickness of about 110 µm to about 140 µm. In certain embodiments, the adhesive polymer matrix has a thickness of about 100 µm. In certain embodiments, the surface of the adhesive polymer matrix opposite the backing layer has a surface area of about 15 $cm^2$.

As described in the general features of transdermal delivery systems, the transdermal delivery systems may optionally comprise an overlay layer and/or a release liner. Accordingly, in certain embodiments, the transdermal delivery system further comprises an overlay layer affixed to the surface of the backing layer opposite the adhesive polymer matrix, wherein the overlay layer is coated with an adhesive and extends beyond the perimeter of part or all of the backing layer and adhesive polymer matrix. In certain embodiments, the transdermal delivery system further comprises a release liner affixed to the surface of the adhesive polymer matrix opposite the backing layer. In certain embodiments, the release liner is a fluoropolymer-coated polyester film.

The backing layer can be one of the backing layers described in the general features of transdermal delivery devices. In certain embodiments, the backing layer is a laminate comprising a polyester film and an ethylene vinyl acetate copolymer film.

Another aspect of the invention provides a transdermal delivery system, comprising an overlay lay affixed to an adhesive polymer matrix, wherein the adhesive polymer matrix comprises:
a. about 0.5% (w/w) to about 10% (w/w) of a first penetration enhancer selected from the group consisting of levulinic acid and a pharmaceutically acceptable salt thereof;
b. about 0.5% (w/w) to about 10% (w/w) of a second penetration enhancer selected from the group consisting of glyceryl monooleate and lauryl lactate;
c. an adhesive polymer;
d. a humectant;
e. levonorgestrel; and
f. ethinyl estradiol.

The description above describes multiple embodiments relating to transdermal delivery systems. The patent application specifically contemplates all combinations of the embodiments. For example, the invention contemplates a transdermal delivery system comprising an overlay lay affixed to an adhesive polymer matrix (as recited in the preceding paragraph) where the adhesive polymer is an acrylate-vinylacetate copolymer.

Exemplary Transdermal Delivery Systems Containing Lactic Acid or a Pharmaceutically Acceptable Salt Thereof Another aspect of the invention provides a transdermal delivery system, comprising a backing layer affixed to an adhesive polymer matrix, wherein the adhesive polymer matrix comprises:
a. about 0.5% (w/w) to about 10% (w/w) of a first penetration enhancer selected from the group consisting of lactic acid and a pharmaceutically acceptable salt thereof;
b. about 0.5% (w/w) to about 10% (w/w) of a second penetration enhancer selected from the group consisting of glyceryl monooleate and lauryl lactate;
c. an adhesive polymer;
d. a humectant;
e. levonorgestrel; and
f. ethinyl estradiol.

In certain embodiments, the adhesive polymer matrix further comprises from about 0.5% (w/w) to about 15% (w/w) of isopropyl myristate.

Another aspect of the invention provides a transdermal delivery system, comprising a backing layer affixed to an adhesive polymer matrix, wherein the adhesive polymer matrix comprises:
a. about 0.5% (w/w) to about 10% (w/w) of a first penetration enhancer that is lactic acid;
b. about 0.5% (w/w) to about 10% (w/w) of a second penetration enhancer that is levulinic acid;
c. an adhesive polymer;
d. a humectant;

e. levonorgestrel; and f. ethinyl estradiol.

In certain embodiments, the adhesive polymer matrix further comprises from about 0.5% (w/w) to about 15% (w/w) of isopropyl myristate.

The description above describes multiple embodiments relating to transdermal delivery systems, such as the amount and identity of the first penetration enhancer, second penetration enhancer, adhesive polymer, humectant, amount of levonorgestrel, and amount of ethinyl estradiol. These embodiments are reiterated here for the exemplary transdermal delivery systems containing lactic acid or a pharmaceutically acceptable salt thereof. The patent application specifically contemplates all combinations of the embodiments.

III. THERAPEUTIC APPLICATIONS

One aspect of the invention provides a method of transdermally administering a medicinal agent to a subject. The method comprising applying a transdermal delivery system described herein containing a medicinal agent to the skin of the subject.

Another aspect of the invention provides a method of transdermally administering levonorgestrel and ethinyl estradiol to a subject. The method comprises applying a transdermal delivery system described herein containing levonorgestrel and ethinyl estradiol to the skin of the subject.

Another aspect of the invention provides a method of controlling fertility in a female subject. The method comprises applying a transdermal delivery system described herein containing levonorgestrel and ethinyl estradiol to the skin of the female subject. In certain embodiments, the transdermal delivery system is replaced once each week for at least three successive weeks.

IV. KITS FOR USE IN MEDICAL APPLICATIONS

Another aspect of the invention provides a kit. The kit comprises: (i) a transdermal delivery system described herein, and (ii) instructions for use, such as in controlling fertility in a female subject.

The description above describes multiple aspects and embodiments of the invention, including transdermal delivery systems, methods of using the transdermal delivery systems, and kits. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and are not intended to limit the invention.

Example 1

Preparation of Transdermal Delivery Systems Containing the Penetration Enhancers Levulinic Acid, Glyceryl Monooleate, and/or Isopropyl Myristate Transdermal delivery systems for administration of levonorgesterel and ethinyl estradiol were prepared and tested as described below. The adhesive polymer matrix contained levulinic acid, glyceryl monooleate, and/or isopropyl myristate.

Experimental Procedure:

Part I: Preparation of Transdermal Delivery Systems

Levonorgesterel and ethinyl estradiol were added to a mixture of ethanol and PVP/VA S-630 (a water-soluble, thermoplastic copolymer of vinylpyrrolidone and vinyl acetate where the copolymer contains approximately 60% vinyl pyrrolidone and 40% vinyl acetate). The resulting combination was mixed until the components were fully dissolved. Next, the penetration enhancer(s) (levulinic acid, glyceryl monooleate, and/or isopropyl myristate) were added to the mixture and resulting mixture was mixed. Then, the adhesive polymer sold by Henkel Corporation under the tradename Duro-Tak 87-4098 (an acrylate-vinylacetate copolymer) was added to the mixture to form an adhesive polymer matrix pre-mix. The weight percentage of components in the adhesive polymer matrix pre-mix (that is, prior to the cast step described below) for each of Formulations A through I is provided in Table 1 below.

TABLE 1

| | ADHESIVE POLYMER MATRIX PRE-MIX FOR FORMULATIONS A-I | | | | | | | | |
|---|---|---|---|---|---|---|---|---|---|
| | Formulation (ingredient w/w %) | | | | | | | | |
| Ingredient | A | B | C | D | E | F | G | H | I |
| Levulinic acid | 0 | 0 | 0 | 0 | 1.5 | 3 | 3 | 3 | 3 |
| Isopropyl myristate | 0 | 3.5 | 0 | 3.5 | 1.75 | 0 | 3.5 | 0 | 3.5 |
| Glyceryl monooleate | 0 | 0 | 3 | 3 | 1.5 | 0 | 0 | 3 | 3 |
| Ethanol | 8 | 8 | 8 | 8 | 8 | 8 | 8 | 8 | 8 |
| PVP/VA S-630 | 1.25 | 1.25 | 1.25 | 1.25 | 1.25 | 1.25 | 1.25 | 1.25 | 1.25 |
| Levonorgesterel | 0.32 | 0.32 | 0.32 | 0.32 | 0.32 | 0.32 | 0.32 | 0.32 | 0.32 |
| Ethinyl estradiol | 0.28 | 0.28 | 0.28 | 0.28 | 0.28 | 0.28 | 0.28 | 0.28 | 0.28 |
| Duro TAK 87-4098 | 90.15 | 86.65 | 87.15 | 83.65 | 85.4 | 87.15 | 83.65 | 84.15 | 80.65 |

The adhesive polymer matrix pre-mix was cast at a thickness of 400 μm onto a release liner (a siliconized polyester sheet sold under the tradename Scotchpak 1022). The pre-mix was dried for 12 minutes at 40° C. in a drying oven to produce an adhesive polymer matrix having a thickness is approximately 100 μm. The weight percentage of components in the adhesive polymer matrix for each of Formulations A through I is provided in Table 2 below. The adhesive polymer matrix was laminated with a backing layer (a poly(ethylene terephthalate) film sold under the tradename Scotchpak 9732).

TABLE 2

ADHESIVE POLYMER MATRIX FOR FORMULATIONS A-I

| Ingredient | Formulation (ingredient w/w %) | | | | | | | | |
|---|---|---|---|---|---|---|---|---|---|
| | A | B | C | D | E | F | G | H | I |
| Levulinic acid | 0.00 | 0.00 | 0.00 | 0.00 | 3.57 | 7.14 | 6.87 | 6.97 | 6.86 |
| Isopropyl myristate | 0.00 | 8.95 | 0.00 | 10.52 | 5.23 | 0.00 | 8.48 | 0.00 | 7.60 |
| Glyceryl monooleate | 0.00 | 0.00 | 8.38 | 8.55 | 3.57 | 0.00 | 0.00 | 7.11 | 7.27 |
| PVP/VA S-630* | 3.125 | 3.125 | 3.125 | 3.125 | 3.125 | 3.125 | 3.125 | 3.125 | 3.125 |
| Ethinyl estradiol | 0.63 | 0.73 | 0.66 | 0.64 | 0.64 | 0.62 | 0.63 | 0.64 | 0.62 |
| Levonorgesterel | 0.72 | 0.78 | 0.69 | 0.74 | 0.71 | 0.70 | 0.69 | 0.72 | 0.68 |
| Duro TAK 87-4098* | 95.52 | 86.41 | 87.15 | 76.43 | 83.16 | 88.42 | 80.21 | 81.44 | 73.83 |

*Estimated w/w percentage based on the total weight of the adhesive polymer matrix, amount of other ingredients in the adhesive polymer matrix, and amount of PVP/VA S-630 and Duro TAK 87-4098 in the adhesive polymer matrix pre-mix used to prepare the adhesive polymer matrix.

Part II: Testing of Transdermal Delivery Systems in Transdermal Flux Tests

To assay transdermal flux of levonorgestrel and ethinyl estradiol across the skin barrier, traditional Franz diffusion cells were used. Human cadaver skin epidermis was used as the substrate throughout all flux experiments to mimic in vivo conditions.

Prior to beginning the diffusion experiment, human cadaver epidermis was separated from underlying dermal tissue by floating the skin sample on 60° C. water for 2 minutes, followed by gently pealing the epidermis away from the dermal tissue with a spatula. The resulting epidermal tissue is then cut into squares having an approximate size of 2 cm×2 cm. Patch samples were then prepared by die-cutting the patches with a ⅝" punch and arbor press. The release liner of the punched sample was then removed and the patch sample was placed on top of the epidermis with the drug adhesive layer contacting the stratum corneum. Gentle pressure was applied to the patch sample to achieve good contact between the adhesive layer and the stratum corneum.

Franz diffusion cells were assembled by placing the epidermis-patch samples between the receptor and donor chambers of the diffusion cell and clamping the chambers together with a pinch clamp. The receptor chamber was filled with phosphate buffered saline solution at pH 7.4 with 0.2% (w/w) $NaN_3$ added as a preservative and 2% (w/w) beta-hydroxypropylcylclodextrin added to ensure sink conditions of the receptor fluid throughout the experiment. In addition, a stir bar was added to each receptor chamber. Care was taken to ensure any air bubbles underneath the skin were removed prior to beginning the flux study. The assembled diffusion cells were then placed in a stirring dry bath heater. The receptor chambers were continually stirred throughout the experiment and the temperature maintained at 32° C. Samples were taken at regular intervals over a period seven of days with fresh receptor solution being used to replace the removed sample aliquot. Sample aliquots were analyzed via high performance liquid chromatography (HPLC) with a gradient method using water (with 0.01% (w/w) formic acid) and acetonitrile (with 0.006% (w/w) formic acid) as the mobile phases, an Eclipse Plus C8 column, and ultraviolet (UV) detection at 220 nm. Flux values were calculated from the slopes of cumulative amounts of the drug in the receptor compartment versus time.

Results:

The transdermal flux of levonorgestrel for each of Formulations A through I is provided in Table 3 below. The data in Table 3 show that each of levulinic acid, glyceryl monooleate, and/or isopropyl myristate increase the flux of levonorgestrel relative to control Formulation A (which does not contain levulinic acid, glyceryl monooleate, or isopropyl myristate). Formulation I containing levulinic acid, glyceryl monooleate, and isopropyl myristate produced the greatest flux of levonorgestrel of Formulations A-I. The Enhancement Ratio (ER) provided in Table 3 is a measure of the increase in levonorgestrel flux of each formulation relative to control Formulation A. Glyceryl monooleate caused a larger increase in the flux of levonorgestrel than levulinic acid. Levulinic acid produced a larger increase in flux of levonorgestrel than isopropyl myristate.

TABLE 3

FLUX OF LEVONORGESTREL FROM FORMULATIONS A-I

| Time (hr) | Formulation (flux of levonorgestrel in µg/cm$^2$) | | | | | | | | |
|---|---|---|---|---|---|---|---|---|---|
| | A | B | C | D | E | F | G | H | I |
| 0 | 0.00 | 0.00 | 0.00 | 0.00 | 0.00 | 0.00 | 0.00 | 0.00 | 0.00 |
| 28 | 0.87 ± 0.06 | 1.04 ± 0.12 | 1.66 ± 0.25 | 2.00 ± 0.08 | 2.26 ± 0.17 | 2.02 ± 0.23 | 2.48 ± 0.13 | 4.30 ± 0.29 | 5.20 ± 0.18 |
| 62 | 1.88 ± 0.10 | 2.44 ± 0.26 | 4.38 ± 0.73 | 5.42 ± 0.16 | 5.30 ± 0.30 | 4.67 ± 0.16 | 5.74 ± 0.18 | 10.41 ± 0.50 | 11.84 ± 0.35 |
| 110 | 3.24 ± 0.13 | 4.37 ± 0.39 | 8.91 ± 1.52 | 10.61 ± 0.28 | 9.16 ± 0.53 | 7.85 ± 0.32 | 9.51 ± 0.25 | 18.26 ± 0.67 | 21.15 ± 0.36 |
| 134 | 3.85 ± 0.17 | 5.37 ± 0.46 | 11.19 ± 1.93 | 13.29 ± 0.30 | 10.81 ± 0.65 | 9.23 ± 0.43 | 11.09 ± 0.36 | 21.88 ± 0.83 | 24.96 ± 0.68 |
| 164 | 4.62 ± 0.20 | 6.53 ± 0.52 | 14.53 ± 2.45 | 16.67 ± 0.37 | 13.44 ± 0.81 | 11.04 ± 0.54 | 13.15 ± 0.41 | 26.61 ± 0.91 | 30.04 ± 0.70 |
| ER at 164 hr | 1.00 | 1.41 | 3.15 | 3.61 | 2.91 | 2.39 | 2.84 | 5.76 | 6.50 |

The transdermal flux of ethinyl estradiol for each of Formulations A through I is provided in Table 4 below. The data in Table 4 show that each of levulinic acid, glyceryl monooleate, and/or isopropyl myristate increase the flux of ethinyl estradiol relative to control Formulation A (which does not contain levulinic acid, glyceryl monooleate, or isopropyl myristate). Formulation I containing levulinic acid, glyceryl monooleate, and isopropyl myristate produced the greatest flux of ethinyl estradiol of Formulations A-I. The Enhancement Ratio (ER) provided in Table 4 is a measure of the increase in ethinyl estradiol flux of each formulation relative to control Formulation A.

TABLE 4

FLUX OF ETHINYL ESTRADIOL FROM FORMULATIONS A-I

| Time | Formulation (flux of ehinyl estradiol in μg/cm$^2$) | | | | | | | | |
|---|---|---|---|---|---|---|---|---|---|
|  | A | B | C | D | E | F | G | H | I |
| 0 | 0.00 | 0.00 | 0.00 | 0.00 | 0.00 | 0.00 | 0.00 | 0.00 | 0.00 |
| 28 | 0.27 ± 0.06 | 0.47 ± 0.17 | 0.62 ± 0.12 | 0.96 ± 0.06 | 0.86 ± 0.07 | 0.76 ± 0.07 | 1.01 ± 0.05 | 1.62 ± 0.11 | 2.22 ± 0.06 |
| 62 | 0.63 ± 0.04 | 1.21 ± 0.33 | 2.19 ± 0.59 | 2.65 ± 0.15 | 2.15 ± 0.15 | 1.71 ± 0.13 | 2.26 ± 0.07 | 4.04 ± 0.22 | 5.50 ± 0.30 |
| 110 | 1.17 ± 0.06 | 2.14 ± 0.51 | 5.14 ± 1.57 | 5.25 ± 0.26 | 3.86 ± 0.26 | 3.04 ± 0.30 | 3.85 ± 0.14 | 7.57 ± 0.37 | 10.92 ± 0.77 |
| 134 | 1.44 ± 0.07 | 2.68 ± 0.58 | 6.45 ± 1.82 | 6.70 ± 0.30 | 4.76 ± 0.36 | 3.66 ± 0.39 | 4.61 ± 0.18 | 9.45 ± 0.47 | 13.24 ± 1.43 |
| 164 | 1.68 ± 0.07 | 3.24 ± 0.64 | 8.77 ± 2.71 | 8.36 ± 0.37 | 5.96 ± 0.44 | 4.39 ± 0.48 | 5.40 ± 0.22 | 11.71 ± 0.55 | 16.33 ± 1.72 |
| ER at 164 hr | 1.00 | 1.92 | 5.21 | 4.97 | 3.54 | 2.61 | 3.21 | 6.97 | 9.71 |

Example 2

Preparation of Transdermal Delivery Systems Containing the Penetration Enhancers Levulinic Acid and/or Glyceryl Monooleate Transdermal delivery systems for administration of levonorgesterel and ethinyl estradiol were prepared and tested as described in Example 1, except that the adhesive polymer matrix contained levulinic acid and/or glyceryl monooleate.

The weight percentage of components in the adhesive polymer matrix pre-mix (that is, prior to casting) for each of Formulations C and J through O is provided in Table 5 below.

TABLE 5

ADHESIVE POLYMER MATRIX PRE-MIXES FOR FORMULATIONS C AND J-O

| Ingredient | Formulation (ingredient w/w %) | | | | | | |
|---|---|---|---|---|---|---|---|
|  | C | J | K | L | M | N | O |
| Levulinic acid | 0 | 1 | 1.5 | 2 | 0 | 1.5 | 2 |
| Glyceryl monooleate | 3 | 1 | 1.5 | 2 | 3 | 3 | 3 |
| Ethanol | 8 | 8 | 8 | 8 | 8 | 8 | 8 |
| PVP/VA S-630 | 1.25 | 1.25 | 1.25 | 1.25 | 1.25 | 1.25 | 1.25 |
| Levonorgesterel | 0.32 | 0.32 | 0.32 | 0.32 | 0.32 | 0.32 | 0.32 |
| Ethinyl estradiol | 0.28 | 0.28 | 0.28 | 0.28 | 0.28 | 0.28 | 0.28 |
| Duro TAK 87-4098 | 87.15 | 88.15 | 87.15 | 86.15 | 86.15 | 85.65 | 85.15 |

The weight percentage of components in the adhesive polymer matrix for each of Formulations C and J through O is provided in Table 6 below.

TABLE 6

ADHESIVE POLYMER MATRIX FOR FORMULATIONS C AND J-O

| Ingredient | Formulation (ingredient w/w %) | | | | | | |
|---|---|---|---|---|---|---|---|
|  | C | J | K | L | M | N | O |
| Levulinic acid | 0.00 | 1.94 | 3.51 | 4.51 | 2.42 | 3.28 | 4.00 |
| Glyceryl monooleate | 8.38 | 2.22 | 3.54 | 3.84 | 6.93 | 6.66 | 6.11 |

TABLE 6-continued

ADHESIVE POLYMER MATRIX FOR FORMULATIONS C AND J-O

| Ingredient | Formulation (ingredient w/w %) | | | | | | |
|---|---|---|---|---|---|---|---|
| | C | J | K | L | M | N | O |
| PVP/VA S-630* | 3.125 | 3.125 | 3.125 | 3.125 | 3.125 | 3.125 | 3.125 |
| Ethinyl estradiol | 0.66 | 0.51 | 0.60 | 0.62 | 0.62 | 0.59 | 0.56 |
| Levonargesterel | 0.69 | 0.56 | 0.67 | 0.69 | 0.69 | 0.66 | 0.61 |
| Durd TAK 87-4098* | 87.15 | 91.65 | 88.55 | 87.23 | 86.21 | 85.69 | 85.60 |

*Estimated w/w percentage based on the total weight of the adhesive polymer matrix, amount of other ingredients in the adhesive polymer matrix, and amount of PVP/VA S-630 and Duro TAK 87-4098 in the adhesive polymer matrix pre-mix used to prepare the adhesive polymer matrix.

The transdermal flux of levonorgestrel measured for each of Formulations C and J through O is provided in Table 7 below. Because skin used in the flux assay in Example 2 was from a different human cadaver than that used in Example 1, the measured flux of levonorgestrel for Formulation C in Example 2 is different than the measure measured flux of levonorgestrel for Formulation C in Example 1.

TABLE 7

FLUX OF LEVONORGESTREL FROM FORMULATIONS C AND J-O

| Time | Formulation (flux of levonorgestrel μg/cm$^2$) | | | | | | |
|---|---|---|---|---|---|---|---|
| (hr) | C | J | K | L | M | N | O |
| 24 | 1.18 ± 0.07 | 1.38 ± 0.19 | 1.43 ± 0.11 | 1.36 ± 0.12 | 1.67 ± 0.15 | 2.03 ± 0.08 | 1.99 ± 0.23 |
| 47 | 1.84 ± 0.15 | 2.12 ± 0.11 | 2.49 ± 0.15 | 2.31 ± 0.14 | 2.85 ± 0.32 | 3.74 ± 0.06 | 3.62 ± 0.33 |
| 71 | 2.78 ± 0.29 | 3.05 ± 0.17 | 3.68 ± 0.22 | 3.39 ± 0.18 | 4.40 ± 0.49 | 5.49 ± 0.10 | 5.14 ± 0.45 |
| 117 | 4.61 ± 0.53 | 4.49 ± 0.19 | 5.63 ± 0.37 | 5.30 ± 0.26 | 7.01 ± 0.88 | 8.44 ± 0.23 | 8.73 ± 0.82 |
| 168 | 6.56 ± 0.76 | 6.28 ± 0.18 | 7.63 ± 0.53 | 7.23 ± 0.38 | 9.64 ± 1.40 | 11.37 ± 0.32 | 12.10 ± 1.27 |

Example 3

Preparation of Additional Transdermal Delivery Systems Containing the Penetration Enhancers Levulinic Acid and/or Glyceryl Monooleate Transdermal delivery systems for administration of levonorgesterel and ethinyl estradiol were prepared and tested as described in Example 1, except that the adhesive polymer matrix contained levulinic acid and/or glyceryl monooleate, and pharmaceutical grade PVP/VA S-630 (sold under the tradename Plasdone S-630 by International Specialty Products located at Wayne, N.J.) was used.

The weight percentage of components in the adhesive polymer matrix pre-mix (that is, prior to casting) for each of Formulations P through S is provided in Table 8 below.

TABLE 8

ADHESIVE POLYMER MATRIX PRE-MIXES FOR FORMULATIONS P-S

| Ingredient | Formulation (ingredient w/w %) | | | |
|---|---|---|---|---|
| | P | Q | R | S |
| Levulinic acid | 0 | 3 | 3 | 1.5 |
| Glyceryl monooleate | 2 | 0 | 2 | 1 |
| Ethanol | 8 | 8 | 8 | 8 |
| PVP/VA S-630 | 1.25 | 1.25 | 1.25 | 1.25 |
| Levonorgesterel | 0.32 | 0.32 | 0.32 | 0.32 |
| Ethinyl estradiol | 0.28 | 0.28 | 0.28 | 0.28 |
| Duro TAK 87-4098 | 88.15 | 87.15 | 85.15 | 87.65 |

The weight percentage of components in the adhesive polymer matrix for each of Formulations P through S is provided in Table 9 below.

TABLE 9

ADHESIVE POLYMER MATRIX FOR FORMULATIONS P-S

| Ingredient | Formulation (ingredient w/w %) | | | |
|---|---|---|---|---|
| | P | Q | R | S |
| Levulinic acid | 0.00 | 6.31 | 6.07 | 3.53 |
| Glyceryl monooleate | 5.74 | 0.00 | 4.80 | 3.08 |
| PVP/VA S-630* | 3.125 | 3.125 | 3.125 | 3.125 |
| Ethinyl estradiol | 0.67 | 0.62 | 0.61 | 0.67 |
| Levonorgesterel | 0.77 | 0.70 | 0.67 | 0.77 |
| Duro TAK 87-4098* | 89.69 | 89.23 | 84.72 | 88.82 |

*Estimated w/w percentage based on the total weight of the adhesive polymer matrix, amount of other ingredients in the adhesive polymer matrix, and amount of PVP/VA S-630 and Duro TAK 87-4098 in the adhesive polymer matrix pre-mix used to prepare the adhesive polymer matrix.

The transdermal flux of levonorgestrel measured for each of Formulations P through S is provided in Table 10 below. Formulation R produced the greatest flux of levonorgestrel of Formulations P through S.

TABLE 10

FLUX OF LEVONORGESTREL FROM FORMULATIONS P-S

Formulation (flux of levonorgestrel in μg/cm$^2$)

| Time (hr) | P | Q | R | S |
|---|---|---|---|---|
| 24 | 1.30 ± 0.19 | 2.04 ± 0.16 | 3.06 ± 0.10 | 1.94 ± 0.06 |
| 48 | 2.51 ± 0.36 | 3.46 ± 0.23 | 5.08 ± 0.08 | 3.41 ± 0.10 |
| 70 | 3.84 ± 0.50 | 4.82 ± 0.32 | 6.45 ± 0.49 | 4.82 ± 0.15 |
| 122 | 6.93 ± 1.00 | 7.48 ± 0.53 | 10.49 ± 0.73 | 7.67 ± 0.22 |
| 166 | 9.67 ± 1.44 | 9.78 ± 0.71 | 14.28 ± 1.01 | 10.16 ± 0.31 |

Example 4

Preparation of Transdermal Delivery Systems Containing the Penetration Enhancers Levulinic Acid and/or Lauryl Lactate Transdermal delivery systems for administration of levonorgesterel and ethinyl estradiol were prepared and tested as described below. The adhesive polymer matrix contained levulinic acid and/or lauryl lactate.

Experimental Procedure:

Part I: Preparation of Transdermal Delivery Systems

Levonorgesterel and ethinyl estradiol were added to a mixture of ethanol and PVP/VA S-630 (a water-soluble, thermoplastic copolymer of vinylpyrrolidone and vinyl acetate sold under the tradename Plasdone S-630 by International Specialty Products located at Wayne, N.J. where the copolymer contains approximately 60% vinyl pyrrolidone and 40% vinyl acetate). The resulting combination was mixed until the components were fully dissolved. Next, the penetration enhancer(s) (levulinic acid and/or lauryl lactate) were added to the mixture and resulting combination was mixed. Then, the adhesive polymer sold by Henkel Corporation under the tradename Duro-Tak 87-4098 (an acrylate-vinylacetate copolymer) was added to the mixture to form an adhesive polymer matrix pre-mix. The weight percentage of components in the adhesive polymer matrix pre-mix (that is, prior to the casting step described below) for each of Formulations T through W is provided in Table 11 below.

TABLE 11

ADHESIVE POLYMER MATRIX PRE-MIX FOR FORMULATIONS T-W

Formulation (w/w % ingredient)

| Ingredient | T | U | V | W |
|---|---|---|---|---|
| Lauryl lactate | 0 | 3 | 3 | 0 |
| Levulinic Acid | 0 | 0 | 1.5 | 1.5 |
| Ethanol | 8 | 8 | 8 | 8 |
| PVP/VA S-630 | 1.25 | 1.25 | 1.25 | 1.25 |
| Levonorgesterel | 0.32 | 0.32 | 0.32 | 0.32 |
| Ethinyl estradiol | 0.28 | 0.28 | 0.28 | 0.28 |
| Duro TAK 87-4098 | 90.15 | 87.15 | 85.65 | 88.65 |

The adhesive polymer matrix pre-mix was cast at a thickness of 400 μm onto a release liner (a siliconized polyester sheet sold under the tradename Scotchpak 1022). The pre-mix was dried for 12 minutes at 40° C. in a drying oven to produce an adhesive polymer matrix having a thickness is approximately 100 μm. The weight percentage of components in the adhesive polymer matrix for each of Formulations T through W is provided in Table 12 below.

The adhesive polymer matrix was laminated with a backing layer (a poly(ethylene terephthalate) film sold under the tradename Scotchpak 9732).

TABLE 12

ADHESIVE POLYMER MATRIX FOR FORMULATIONS T-W

Formulation (ingredient w/w %)

| Ingredient | T | U | V | W |
|---|---|---|---|---|
| Lauryl lactate | 0.00 | 9.30 | 8.38 | 0.00 |
| Levulinic Acid | 0.00 | 0.00 | 3.32 | 3.50 |
| PVP/VA S-630* | 3.125 | 3.125 | 3.125 | 3.125 |
| Ethinyl estradiol | 0.68 | 0.70 | 0.63 | 0.66 |
| Levonorgesterel | 0.79 | 0.79 | 0.71 | 0.74 |
| Duro TAK 87-4098* | 95.40 | 86.09 | 83.83 | 91.97 |

*Estimated w/w percentage based on the total weight of the adhesive polymer matrix, amount of other ingredients in the adhesive polymer matrix, and amount of PVP/VA S-630 and Duro TAK 87-4098 in the adhesive polymer matrix pre-mix used to prepare the adhesive polymer matrix.

Part II: Testing of Transdermal Delivery Systems in Transdermal Flux Tests

Transdermal flux assays measuring the flux of levonorgestrel were performed as described in Example 1. The transdermal flux of levonorgestrel for each of Formulations T through W is provided in Table 13 below. The data in Table 13 show that each of levulinic acid and lauryl lactate increase the flux of levonorgestrel relative to control Formulation T (which did not contain levulinic acid or lauryl lactate). Formulation V containing levulinic acid and lauryl lactate produced the greatest flux of levonorgestrel of Formulations T-W. The Enhancement Ratio (ER) provided in Table 13 is a measure of the increase in flux of each formulation relative to control Formulation T. Levulinic acid caused a larger increase in the flux of levonorgestrel than lauryl lactate.

TABLE 13

FLUX OF LEVONORGESTREL FROM FORMULATIONS T-W

Formulation (flux levonorgestrel in μg/cm$^2$)

| Time (hr) | T | U | V | W |
|---|---|---|---|---|
| 0 | 0.00 | 0.00 | 0.00 | 0.00 |
| 23 | 1.40 ± 0.20 | 1.71 ± 0.19 | 2.25 ± 0.09 | 1.82 ± 0.22 |
| 48 | 2.75 ± 0.42 | 3.70 ± 0.44 | 4.62 ± 0.21 | 3.56 ± 0.47 |
| 76 | 4.11 ± 0.65 | 5.74 ± 0.74 | 6.69 ± 0.37 | 5.12 ± 0.68 |
| 120 | 5.90 ± 1.04 | 8.60 ± 1.24 | 9.47 ± 0.65 | 7.15 ± 1.06 |
| 166 | 7.92 ± 1.37 | 12.05 ± 1.79 | 12.73 ± 0.99 | 9.57 ± 1.27 |
| ER at 120 hr | 1.00 | 1.52 | 1.61 | 1.21 |

Example 5

Preparation of Additional Transdermal Delivery Systems Containing the Penetration Enhancers Levulinic Acid, Lauryl Lactate, and/or Glyceryl Monooleate Transdermal delivery systems for administration of levonorgesterel and ethinyl estradiol were prepared and tested as described below. The adhesive polymer matrix contained levulinic acid, lauryl lactate, and/or glyceryl monooleate.

Experimental Procedure:
Part I: Preparation of Transdermal Delivery Systems

PVP/VA S-630 (a water-soluble, thermoplastic copolymer of vinylpyrrolidone and vinyl acetate where the copolymer contains approximately 60% vinyl pyrrolidone and 40% vinyl acetate) was weighed and transferred into a 100 mL capped media bottle. Ethanol was weighed and added to the media bottle. The resulting mixture was agitated with a vortexer until the solution was clear. Levonorgestrel was weighed and added to the media bottle. The resulting mixture was again mixed with a vortexer until clear (~1-2 minutes). Ethinyl estradiol was weighed and added to the media bottle. The resulting mixture was again mixed with a vortexer until clear (~1-2 minutes). Next, the penetration enhancer(s) (levulinic acid, lauryl lactate, and/or glyceryl monooleate) were added to the mixture, and the resulting mixture was mixed with a vortexer for ~1-2 minutes. The mixture was slightly hazy after mixing during this step. For each of the foregoing steps, the media bottle was capped closed while mixing was performed. Then, the adhesive polymer sold by Henkel Corporation under the tradename Duro-Tak 87-4098 (an acrylate-vinylacetate copolymer) was added to the media bottle. The media bottle was then capped using a cap with a hole in the center that allowed the shaft of a three-blade propeller to pass through. Using an overhead stirrer, the contents of the media bottle were then mixed for 5 minutes (the cap limited evaporation during this process). After mixing was complete, the solution was clear. Then, the media bottle was fully sealed and the resulting adhesive polymer matrix pre-mix was allowed to sit overnight at room temperature (RT) to allow any entrapped air to escape.

The weight percentage of components in the adhesive polymer matrix pre-mix (that is, prior to the cast step described below) for each of Formulations A1 through E1 is provided in Table 14 below.

TABLE 14

ADHESIVE POLYMER MATRIX PRE-MIX FOR FORMULATIONS A1-E1

| Ingredient | Formulation (ingredient w/w %) | | | | |
|---|---|---|---|---|---|
| | A1 | B1 | C1 | D1 | E1 |
| Lauryl lactate | 3 | 0 | 0 | 3 | 0 |
| Levulinic acid | 1.5 | 1.5 | 0 | 1.5 | 1.5 |
| Glyceryl monooleate | 0 | 1 | 0 | 0 | 1 |
| Ethanol | 8 | 8 | 10.5 | 8 | 8 |
| PVP/VA S-630 | 1.25 | 1.25 | 1.25 | 1.25 | 1.25 |
| Levonorgesterel | 0.32 | 0.32 | 0.32 | 0 | 0 |
| Ethinyl estradiol | 0.336 | 0.336 | 0.336 | 0 | 0 |
| Duro TAK 87-4098 | 85.65 | 87.594 | 87.594 | 86.25 | 88.25 |

The adhesive polymer matrix pre-mix (5 mL) was cast at a thickness of 400 μm onto a release liner (a siliconized polyester sheet sold under the tradename Scotchpak 1022). The pre-mix was dried for 12 minutes at 40° C. in a drying oven to produce an adhesive polymer matrix. Once the adhesive polymer matrix was dried, it was allowed to equilibrate for 10 minutes at room temperature. The adhesive polymer matrix resulting from Formulation A1 had a thickness of 126 μm. The adhesive polymer matrix resulting from Formulation B1 had a thickness of 130 μm.

The adhesive polymer matrix was laminated with a backing layer (a poly(ethylene terephthalate) film sold under the tradename Scotchpak 9732) with the polyester side affixed to the patch. The weight percentage of components in the adhesive polymer matrix of Formulations A1 and B1 is provided in Table 15 below.

TABLE 15

ADHESIVE POLYMER MATRIX FOR FORMULATIONS A1 AND B1

| Ingredient | Formulation (ingredient w/w %) | |
|---|---|---|
| | A1 | B1 |
| Lauryl lactate | 7.38 | 0 |
| Levulinic acid | 3.47 | 3.64 |
| Glyceryl monooleate | 0 | 2.30 |
| PVP/VA S-630* | 3 | 3 |
| Levonorgesterel | 0.77 | 0.82 |
| Ethinyl estradiol | 0.82 | 0.87 |
| Duro TAK 87-4098* | 84.5 | 89.4 |

*Estimated w/w percentage based on the total weight of the adhesive polymer matrix, amount of other ingredients in the adhesive polymer matrix, and amount of PVP/VA S-630 and Duro TAK 87-4098 in the adhesive polymer matrix pre-mix used to prepare the adhesive polymer matrix.

Part II: Testing of Transdermal Delivery Systems in Transdermal Flux Tests

To assay transdermal flux of levonorgestrel and ethinyl estradiol across the skin barrier, traditional Franz diffusion cells (FDCs) were used. Human cadaver skin epidermis was used as the substrate throughout all flux experiments to mimic in vivo conditions.

Intact human cadaver skin was purchased from Allosource (Centennial, Colo.). Skin was dermatomed by Allosource to a thickness of ~500 μm. Donor criteria was limited to: race: Caucasian, age: 30-70 yrs old, donor site: thigh or posterior torso, cause of death: no diseases, cancer, or chemotherapy that would compromise skin. When the skin was received, it was stored at −20° C. until the morning of the study. The skin was then removed from the freezer and allowed to defrost at room temperature. After being thoroughly defrosted, the skin was heat-separated by floating in a 60° C. water bath for 2 minutes, removing the skin and then separating the epidermis from the underlying dermal tissue with a spatula. The separated epidermis was then tapped dry, rinsed with phosphate buffered saline (PBS) and tapped dry again.

The epidermis was then cut into ~2 cm×2 cm squares and mounted in FDCs. FDCs with a 3.3 mL receiver volume and 0.55 cm$^2$ diffusional area were used. Receptor wells were filled with isotonic PBS at pH 7.4 containing 0.1% $NaN_3$ and 1% hydroxypropyl betacyclodextrin (HPBCD). The HPBCD was added to the receptor fluid to ensure sink conditions for the actives throughout the experiment. A stir bar was added to each receptor well. Prior to assembling the FDC, prototype patches were punched to size using a ⅝" diameter punch, the release liner removed and the patch firmly affixed to the center of the skin piece. Once the patch was in place, the donor cell flanges were coated with a thin bead of vacuum grease and centered over the skin piece. The vacuum grease grips the skin and allowed for ease of FDC assembly. The donor cells were then aligned over the receptor cells and the two cells clamped together using a pinch clamp. The FDCs were then placed into stirring dry block heaters. The receptor fluid was continuously stirred and maintained at 32±0.5° C. throughout the experiment. At varying time points across a 7 day period, sample aliquots were drawn and the sample volume replaced with fresh buffer. Samples were analyzed via high-performance liquid chromatograph (HPLC). Flux values of actives (i.e., levonorgestrel and ethinyl estradiol) were calculated from the slopes of cumulative amounts of the drug in the receptor compartment versus time.

Figure 2:
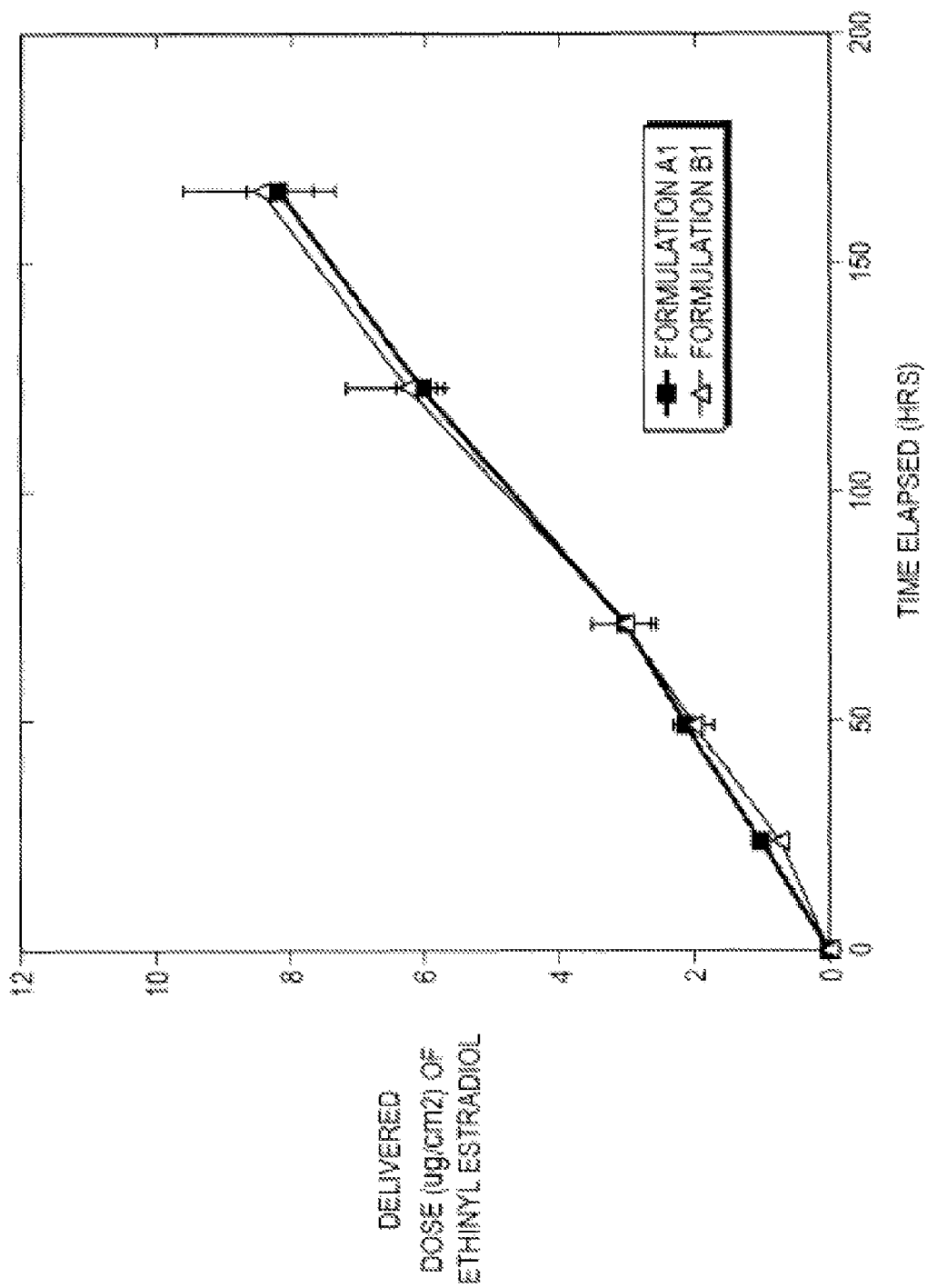
FIG. 2 is a graph showing the delivered dose of ethinyl estradiol as a function of time in the transdermal flux test described in Example 5.

Results:

The transdermal flux of levonorgestrel for Formulations A1 and B1 is provided in FIG. 1. The transdermal flux of ethinyl estradiol for Formulations A1 and B1 is provided in FIG. 2. Each data point in FIGS. 1 and 2 is an average of ten replicates on each of three donor skins for a total of thirty replicates per data point.

Part III: Stability Testing of Transdermal Delivery Systems

To analyze stability of the transdermal delivery systems, five patches were prepared for each formulation (i.e., Formulations A1, B1, C1, D1, and E1) and placed in stability chambers at 25° C./60% relative humidity. Samples of each patch were analyzed at the beginning of the experiment (i.e., T=0) and after storage for 1 month, 3 months, and 6 months for the amount of ethinyl estradiol, levonorgesterel, lauryl lactate, glyceryl monooleate, levulinic acid, and impurities relating to ethinyl estradiol and levonorgesterel. The symbol "N/A" indicates not applicable. Results of the stability study are provided in Tables 16-21.

TABLE 16

PERCENT RECOVERY OF ETHINYL ESTRADIOL (EE)

| Formulation | Percent at T = 0 (±SD) (%) | Percent Recovery of EE (relative to initial) (%) | | | |
|---|---|---|---|---|---|
| | | T = 0 | 1 month | 3 months | 6 months |
| A1 | 0.8197 (±0.039) | 100 (±4.72) | 101.12 (±3.30) | 103.10 (±6.81) | 106.91 (±5.87) |
| B1 | 0.8701 (±0.015) | 100 (±1.70) | 97.92 (±0.763) | 98.89 (±0.681) | 98.77 (±0.56) |
| C1 | 0.962 (±0.023) | 100 (±2.36) | 99.74 (±2.12) | 100.46 (±4.21) | 101.21 (±2.96) |
| D1 | 0.000 (±0.000) | N/A | N/A | N/A | N/A |
| E1 | 0.000 (±0.000) | N/A | N/A | N/A | N/A |

TABLE 17

PERCENT RECOVERY OF LEVONORGESTREL (LN)

| Formulation | Percent at T = 0 (±SD) (%) | Percent Recovery of LN (relative to initial) (%) | | | |
|---|---|---|---|---|---|
| | | T = 0 | 1 month | 3 months | 6 months |
| A1 | 0.7715 (±0.033) | 100 (±4.25) | 100.89 (±3.29) | 102.57 (±6.74) | 104.10 (±5.91) |
| B1 | 0.8157 (±0.012) | 100 (±1.52) | 97.83 (±0.72) | 98.27 (±0.75) | 96.19 (±0.34) |
| C1 | 0.907 (±0.022) | 100 (±2.39) | 99.99 (±1.47) | 100.55 (±3.54) | 99.63 (±2.08) |
| D1 | 0.000 (±0.000) | N/A | N/A | N/A | N/A |
| E1 | 0.000 (±0.000) | N/A | N/A | N/A | N/A |

TABLE 18

PERCENT RECOVERY OF LAURYL LACTATE (LL)

| Formulation | Percent at T = 0 (±SD) (%) | Percent Recovery of LL (relative to initial) (%) | | | |
|---|---|---|---|---|---|
| | | T = 0 | 1 month | 3 months | 6 months |
| A1 | 7.377 (±0.263) | 100 (±3.56) | 104.28 (±2.38) | 102.72 (±5.18) | 101.00 (±5.50) |
| B1 | 0.000 (±0.000) | N/A | N/A | N/A | N/A |
| C1 | 0.000 (±0.000) | N/A | N/A | N/A | N/A |
| D1 | 7.279 (±0.287) | 100 (±3.94) | 99.92 (±4.39) | 99.19 (±4.00) | 92.81 (±4.35) |
| E1 | 0.000 (±0.000) | N/A | N/A | N/A | N/A |

TABLE 19

PERCENT RECOVERY OF GLYCERYL MONOOLEATE (GM)

| Formulation | Percent at T = 0 (±SD) (%) | Percent Recovery of GM (relative to initial) (%) | | | |
|---|---|---|---|---|---|
| | | T = 0 | 1 month | 3 months | 6 months |
| A1 | 0.000 (±0.000) | N/A | N/A | N/A | N/A |
| B1 | 2.305 (±0.038) | 100 (±1.65) | 103.56 (±4.27) | 97.07 (±0.87) | 100.96 (±0.86) |
| C1 | 0.000 (±0.000) | N/A | N/A | N/A | N/A |
| D1 | 0.000 (±0.000) | N/A | N/A | N/A | N/A |
| E1 | 2.635 (±0.060) | 100 (±2.29) | 102.87 (±2.09) | 100.48 (±0.79) | 98.92 (±3.38) |

TABLE 20

PERCENT RECOVERY OF LEVULINIC ACID (LA)

| Formulation | Percent at T = 0 (±SD) (%) | Percent Recovery of LA (relative to initial) (%) | | | |
|---|---|---|---|---|---|
| | | T = 0 | 1 month | 3 months | 6 months |
| A1 | 3.472 (±0.159) | 100 (±4.58) | 104.82 (±3.62) | 108.79 (±6.29) | 106.09 (±5.38) |
| B1 | 3.644 (±0.065) | 100 (±1.78) | 102.07 (±1.07) | 105.49 (±2.03) | 100.85 (±0.82) |
| C1 | 0.000 (±0.000) | N/A | N/A | N/A | N/A |
| D1 | 3.596 (±0.170) | 100 (±4.73) | 104.09 (±1.90) | 104.83 (±8.05) | 98.83 (±5.93) |
| E1 | 3.928 (±0.112) | 100 (±2.85) | 101.73 (±3.58) | 105.99 (±1.53) | 101.69 (±0.81) |

TABLE 21

PERCENTAGE OF IMPURITIES RELATING TO ETHINYL ESTRADIOL (EE) AND LEVONORGESTREL (LN)

| Formulation | Percent at T = 0 (±SD) (%) | Percent of Impurities Relating to EE and LN (%) | | | |
|---|---|---|---|---|---|
| | | T = 0 | 1 month | 3 months | 6 months |
| A1 | 0.482 (±0.024) | 0.482 (±4.94) | 0.345 (±32.24) | 0.395 (±39.20) | 0.550 (±6.02) |
| B1 | 0.619 (±0.161) | 0.619 (±26.01) | 0.282 (±22.33) | 0.495 (±4.48) | 0.533 (±20.55) |
| C1 | 0.567 (±0.027) | 0.567 (±4.68) | 0.220 (±39.65) | 0.450 (±1.20) | 0.33 (±24.35) |
| D1 | 0.000 (±0.000) | 0.000 (±0.000) | N/A | N/A | N/A |
| E1 | 0.000 (±0.000) | 0.000 (±0.000) | N/A | N/A | N/A |

Example 6

Preparation of Additional Transdermal Delivery Systems Containing the Penetration Enhancers Levulinic Acid, Lauryl Lactate, Glyceryl Monooleate, and/or Isopropyl Myristate Transdermal delivery systems for administration of levonorgesterel and ethinyl estradiol were prepared and tested for stability as described in Example 5, except that (i) the adhesive polymer matrix contained levulinic acid, lauryl lactate, glyceryl monooleate, and/or isopropyl myristate, and (ii) the adhesive polymer matrix pre-mix was cast at a thickness of 700 μm onto the release liner.

The weight percentage of components in the adhesive polymer matrix pre-mix (that is, prior to casting) for each of Formulations F1 through K1 is provided in Table 22 below.

TABLE 22

ADHESIVE POLYMER MATRIX PRE-MIX FOR FORMULATIONS A-I

| Ingredient | Formulation (ingredient w/w %) | | | | | |
|---|---|---|---|---|---|---|
| | F1 | G1 | H1 | I1 | J1 | K1 |
| Lauryl lactate | 3 | 3 | 0 | 0 | 0 | 0 |
| Levulinic acid | 1.5 | 1.5 | 1.5 | 1.5 | 1.5 | 1.5 |
| Propylene glycol | 5 | 0 | 0 | 0 | 0 | 0 |
| Dipropylene glycol | 0 | 2.5 | 0 | 0 | 0 | 0 |
| Glyceryl monooleate | 0 | 0 | 1 | 1 | 0.2 | 0 |
| Isopropyl Myristate | 0 | 0 | 0 | 0 | 3 | 3 |
| Ethanol | 8 | 8 | 8 | 8 | 8 | 8 |
| PVP/VA S-630 | 1.25 | 1.25 | 1.25 | 1.25 | 1.25 | 1.25 |
| Levonorgesterel | 0.32 | 0.32 | 0.32 | 0.32 | 0.32 | 0.32 |

TABLE 22-continued

ADHESIVE POLYMER MATRIX PRE-MIX FOR FORMULATIONS A-I

| Ingredient | Formulation (ingredient w/w %) | | | | | |
|---|---|---|---|---|---|---|
| | F1 | G1 | H1 | I1 | J1 | K1 |
| Ethinyl estradiol | 0.336 | 0.336 | 0.336 | 0.336 | 0.336 | 0.336 |
| Vitamin E | 0 | 0 | 0.04 | 0 | 0 | 0 |
| Ascorbyl palmitate | 0 | 0 | 0 | 0.04 | 0 | 0 |
| Duro Tak 87-4098 | 80.594 | 83.094 | 87.554 | 87.554 | 85.394 | 85.594 |

Part II: Stability Testing of Transdermal Delivery Systems

To analyze stability of the transdermal delivery systems, five patches were prepared for each formulation (i.e., Formulations F1, G1, H1, I1, J1, and K1) and placed in stability chambers at 25° C./60% relative humidity. Samples of each patch were analyzed at the beginning of the experiment (i.e., T=0) and after storage for 1 month and 3 months for the amount of ethinyl estradiol, levonorgesterel, lauryl lactate, glyceryl monooleate, levulinic acid, and impurities relating to ethinyl estradiol and levonorgesterel. The symbol "N/A" indicates not applicable. Results of the stability study are provided in Tables 23-28.

TABLE 23

PERCENT RECOVERY OF ETHINYL ESTRADIOL (EE)

| Formulation | Percent at T = 0 (±SD) (%) | Percent Recovery of EE (relative to initial) (%) | | |
|---|---|---|---|---|
| | | T = 0 | 1 month | 3 months |
| F1 | 0.817 (±0.008) | 100 (±0.95) | 97.96 (±1.02) | 94.86 (±2.01) |
| G1 | 0.82 (±0.008) | 100 (±0.95) | 98.81 (±3.84) | 96.08 (±0.11) |

TABLE 23-continued

PERCENT RECOVERY OF ETHINYL ESTRADIOL (EE)

| Formulation | Percent at T = 0 (±SD) (%) | Percent Recovery of EE (relative to initial) (%) | | |
|---|---|---|---|---|
| | | T = 0 | 1 month | 3 months |
| H1 | 0.835 (±0.009) | 100 (±1.04) | 100.3 (±0.3) | 96.7 (±0.23) |
| I1 | 0.851 (±0.004) | 100 (±0.47) | 97.19 (±1.83) | 94.44 (±0.13) |
| J1 | 0.838 (±0.001) | 100 (±0.16) | 98.86 (±0.62) | 96.41 (±0.63) |
| K1 | 0.826 (±0.001) | 100 (±0.16) | 98.31 (±0.2) | 95.89 (±0.28) |

TABLE 24

PERCENT RECOVERY OF LEVONORGESTREL (LN)

| Formulation | Percent at T = 0 (±SD) (%) | Percent Recovery of LN (relative to initial) (%) | | |
|---|---|---|---|---|
| | | T = 0 | 1 month | 3 months |
| F1 | 0.766 (±0.008) | 100 (±0.99) | 98.2 (±0.87) | 98.46 (±1.53) |
| G1 | 0.746 (±0.006) | 100 (±0.83) | 98.58 (±3.79) | 99.01 (±0.1) |
| H1 | 0.775 (±0.007) | 100 (±0.94) | 100.4 (±0.24) | 99.63 (±0.22) |
| I1 | 0.786 (±0.003) | 100 (±0.35) | 97.44 (±1.92) | 96.81 (±0.37) |
| J1 | 0.775 (±0.002) | 100 (±0.2) | 98.46 (±0.42) | 99.96 (±0.98) |
| K1 | 0.769 (±0.001) | 100 (±0.07) | 98.24 (±0.11) | 99.62 (±0.38) |

TABLE 25

PERCENT RECOVERY OF LAURYL LACTATE (LL)

| Formulation | Percent at T = 0 (±SD) (%) | Percent Recovery of LL (relative to initial) (%) | | |
|---|---|---|---|---|
| | | T = 0 | 1 month | 3 months |
| F1 | 7.27 (±0.06) | 100 (±0.8) | 94.65 (±0.9) | 98.9 (±2.28) |
| G1 | 7.1 (±0.07) | 100 (±1.06) | 96.11 (±3.76) | 100.46 (±0.4) |
| H1 | NA | NA | NA | NA |
| I1 | NA | NA | NA | NA |
| J1 | NA | NA | NA | NA |
| K1 | NA | NA | NA | NA |

TABLE 26

PERCENT RECOVERY OF GLYCERYL MONOOLEATE (GM)

| Formulation | Percent at T = 0 (±SD) (%) | Percent Recovery of GM (relative to initial) (%) | | |
|---|---|---|---|---|
| | | T = 0 | 1 month | 3 months |
| F1 | NA | NA | NA | NA |
| G1 | NA | NA | NA | NA |
| H1 | 2.49 (±0.03) | 100 (±1.18) | 104.28 (±0.94) | 101.49 (±1.68) |
| I1 | 2.55 (±0.05) | 100 (±2.13) | 101.33 (±1.39) | 101.11 (±2.21) |
| J1 | 0.56 (±0) | 100 (±0.43) | 101.82 (±1.24) | 108.34 (±1.51) |
| K1 | NA | NA | NA | NA |

TABLE 27

PERCENT RECOVERY OF LEVULINIC ACID (LA)

| Formulation | Percent at T = 0 (±SD) (%) | Percent Recovery of LA (relative to initial) (%) | | |
|---|---|---|---|---|
| | | T = 0 | 1 month | 3 months |
| F1 | 3.66 (±0.09) | 100 (±2.42) | 96.6 (±1.55) | 91.48 (±3.21) |
| G1 | 3.65 (±0.03) | 100 (±0.89) | 99.26 (±2.74) | 98.56 (±0.86) |

TABLE 27-continued

PERCENT RECOVERY OF LEVULINIC ACID (LA)

| Formulation | Percent at T = 0 (±SD) (%) | Percent Recovery of LA (relative to initial) (%) | | |
|---|---|---|---|---|
| | | T = 0 | 1 month | 3 months |
| H1 | 3.7 (±0.07) | 100 (±1.92) | 101.54 (±0.66) | 98.62 (±0.17) |
| I1 | 4.28 (±0.03) | 100 (±0.63) | 98.95 (±2.38) | 96.57 (±2.13) |
| J1 | 3.86 (±0.03) | 100 (±0.73) | 99.81 (±1.97) | 100.47 (±1.34) |
| K1 | 3.65 (±0.02) | 100 (±0.59) | 99.44 (±2.49) | 97.96 (±1.48) |

TABLE 28

PERCENTAGE OF IMPURITIES RELATING TO ETHINYL ESTRADIOL (EE) AND LEVONORGESTREL (LN)

| Formulation | Percent at T = 0 (±SD) (%) | Percent of Impurities Relating to EE and LN (%) | | |
|---|---|---|---|---|
| | | T = 0 | 1 month | 3 months |
| F1 | 0.42 (±0.05) | 0.42 (±11.65) | 0.45 (±4.11) | 0.54 (±1.11) |
| G1 | 0.42 (±0.02) | 0.42 (±3.61) | 0.43 (±8.83) | 0.57 (±0.9) |
| H1 | 0.41 (±0.01) | 0.41 (±3.27) | 0.72 (±4.76) | 0.74 (±3.11) |
| I1 | 0.4 (±0.01) | 0.4 (±1.67) | 0.18 (±21.66) | 1.32 (±1.75) |
| J1 | 0.41 (±0.03) | 0.41 (±6.55) | 0.4 (±7.66) | 0.59 (±7.12) |
| K1 | 0.43 (±0.02) | 0.43 (±4.95) | 0.38 (±6.49) | 0.46 (±1.77) |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A transdermal delivery system, comprising a backing layer affixed to an adhesive polymer matrix, wherein the adhesive polymer matrix comprises:
   a. about 3% (w/w) to about 5% (w/w) of a first penetration enhancer selected from the group consisting of levulinic acid and a pharmaceutically acceptable salt thereof;
   b. about 0.5% (w/w) to about 10% (w/w) of a second penetration enhancer selected from the group consisting of glyceryl monooleate and lauryl lactate;
   c. about 80% (w/w) to about 92% (w/w) of an adhesive polymer;
   d. a humectant;
   e. about 0.6% (w/w) to about 1.0% (w/w) levonorgestrel; and
   f. about 0.6% (w/w) to about 1.0% (w/w) ethinyl estradiol.

2. The transdermal delivery system of claim 1, wherein the first penetration enhancer is levulinic acid.

3. The transdermal delivery system of claim 2, wherein the second penetration enhancer is glyceryl monooleate.

4. The transdermal delivery system of claim 2, wherein the second penetration enhancer is lauryl lactate.

5. The transdermal delivery system of claim 1, wherein the adhesive polymer matrix comprises from about 3.5% (w/w) to about 4.0% (w/w) of the first penetration enhancer.

6. The transdermal delivery system of claim 1, wherein the adhesive polymer matrix comprises from about 2.0% (w/w) to about 3.0% (w/w) of the second penetration enhancer.

7. The transdermal delivery system of claim 1, wherein the adhesive polymer matrix comprises from about 2.25% (w/w) to about 2.75% (w/w) of the second penetration enhancer.

8. The transdermal delivery system of claim 1, wherein the adhesive polymer matrix comprises from about 7.0% (w/w) to about 8.0% (w/w) of the second penetration enhancer.

9. The transdermal delivery system of claim 1, wherein the adhesive polymer is a polyacrylate copolymer.

10. The transdermal delivery system of claim 1, wherein the adhesive polymer is a random copolymer of 2-ethylhexyl acrylate and vinyl acetate.

11. The transdermal delivery system of claim 1, wherein the adhesive polymer matrix comprises from about 88% (w/w) to about 90% (w/w) adhesive polymer.

12. The transdermal delivery system of claim 1, wherein the humectant comprises a polyvinylpyrrolidone copolymer.

13. The transdermal delivery system of claim 1, wherein the adhesive polymer matrix comprises from about 2.75% (w/w) to about 3.75% (w/w) humectant.

14. The transdermal delivery system of claim 1, formulated for delivery of ethinyl estradiol and levonorgestrel, wherein the ethinyl estradiol is transdermally delivered at a rate of from about 5 μg to about 25 μg per day for a term of about seven days, and the levonorgestrel is transdermally delivered at a rate of about 25 μg to about 35 μg per day for a term of about seven days.

15. The transdermal delivery system of claim 1, formulated for delivery of ethinyl estradiol and levonorgestrel, wherein the ethinyl estradiol is transdermally delivered at a rate of from about 10 μg to about 20 μg per day for a term of about seven days, and the levonorgestrel is transdermally delivered at a rate of about 30 μg per day for a term of about seven days.

16. The transdermal delivery system of claim 1, wherein the levonorgestrel is transdermally delivered in an amount sufficient to produce a serum concentration of at least 1,000 pg/mL in a human.

17. The transdermal delivery system of claim 1, wherein the adhesive polymer matrix has a thickness of about 50 μm to about 150 μm.

18. The transdermal delivery system of claim 1, wherein the adhesive polymer matrix has a thickness of about 100 μm.

19. A method of controlling fertility in a female subject, comprising applying a transdermal delivery system of claim 1 to the skin of the female subject.

20. The method of claim 19, wherein the transdermal delivery system is replaced once each week for at least three successive weeks.

21. The method of claim 20, wherein the transdermal delivery system comprises a backing layer affixed to an adhesive polymer matrix, wherein the adhesive polymer matrix comprises:
   a. about 3.5% (w/w) to about 4% (w/w) of a first penetration enhancer selected from the group consisting of levulinic acid and a pharmaceutically acceptable salt thereof;
   b. about 2.2% (w/w) to about 2.8% (w/w) of a second penetration enhancer that is glyceryl monooleate;
   c. about 86% (w/w) to about 90% (w/w) of an adhesive polymer that is a random copolymer of 2-ethylhexyl acrylate and vinyl acetate;
   d. about 2% (w/w) to about 4% (w/w) of a humectant that is a copolymer of vinylpyrrolidone and vinyl acetate;
   e. about 0.7% (w/w) to about 0.9% (w/w) levonorgestrel; and
   f. about 0.7% (w/w) to about 0.9% (w/w) ethinyl estradiol.

22. The method of claim 20, wherein the transdermal delivery system comprises a backing layer affixed to an adhesive polymer matrix, wherein the adhesive polymer matrix comprises:
   a. about 3.5% (w/w) to about 4% (w/w) levulinic acid;
   b. about 6% (w/w) to about 9% (w/w) lauryl lactate;
   c. about 80% (w/w) to about 88% (w/w) of an adhesive polymer that is an acrylate-vinylacetate copolymer;
   d. about 2% (w/w) to about 4% (w/w) of a humectant that is a copolymer of vinylpyrrolidone and vinyl acetate;
   e. about 0.7% (w/w) to about 0.9% (w/w) levonorgestrel; and
   f. about 0.7% (w/w) to about 0.9% (w/w) ethinyl estradiol.

* * * * *